(12) United States Patent
Prasse et al.

(10) Patent No.: US 12,036,218 B2
(45) Date of Patent: Jul. 16, 2024

(54) MODULATORS OF AIRWAY BASAL CELLS FOR THE TREATMENT OR PREVENTION OF LUNG DISEASES

(71) Applicant: Fraunhofer Gesellschaft zur Förderung der angewandten Forschung e.V., Munich (DE)

(72) Inventors: Antje Prasse, Freiburg (DE); Jonas Schupp, New Haven, CT (US)

(73) Assignee: Fraunhofer-Gesellschaft zur Förderung der angewandten Forschung e. V., Munich (DE)

( * ) Notice: Subject to any disclaimer, the term of this patent is extended or adjusted under 35 U.S.C. 154(b) by 0 days.

(21) Appl. No.: 17/465,087

(22) Filed: Sep. 2, 2021

(65) Prior Publication Data

US 2022/0062269 A1 Mar. 3, 2022

(30) Foreign Application Priority Data

Sep. 2, 2020 (EP) .................................... 20194132

(51) Int. Cl.
*A61K 31/4706* (2006.01)
*A61P 11/00* (2006.01)
*G01N 33/68* (2006.01)

(52) U.S. Cl.
CPC .......... *A61K 31/4706* (2013.01); *A61P 11/00* (2018.01); *G01N 33/6893* (2013.01); *G01N 2800/12* (2013.01)

(58) Field of Classification Search
CPC ................................................. A61K 31/4706
See application file for complete search history.

(56) References Cited

FOREIGN PATENT DOCUMENTS

| WO | 2014/144121 | A2 | | 9/2014 | | |
|---|---|---|---|---|---|---|
| WO | 2014/144121 | A3 | | 9/2014 | | |
| WO | 2014/144121 | A9 | | 9/2014 | | |
| WO | WO2014/144121 | | * | 9/2014 | ............... | C12Q 1/68 |

OTHER PUBLICATIONS

Hu et al., J'nal of Pharmacology & Experimental Theapeutics (2014) vol. 31 (1).*
Yin-Ying et al Scientific Reports, vol. 7(1) 2017.*
Wollin et al. European Respiratory J'nal, vol. 45(5) (2015).*
Hu Meng et al., "Therapeutic targeting of SRC kinase in myofibroblast differentiation and pulmonary fibrosis", Journal of Pharmacology and Experimental Therapeutics, vol. 351, No. 1, pp. 87-95, Sep. 30, 2014.
Lu Yin-Ying et al., "Interaction of Src and Alpha-V Integrin Regulates Fibroblast Migration and Modulates LungFibrosis in a Preclinical Model of LungFibrosis", Scientific Reports, vol. 7, No. 1, pp. 46357-1, Apr. 11, 2017.
Lutz Wollin et al., "Mode of action of nintedanib in the treatment of idiopathic pulmonary fibrosis", European Respiratory Journal, vol. 45, No. 5, pp. 1434-1445, May 30, 2015.
Extended European Search Report, European Patent Application No. 20194132.5, Feb. 3, 2021 (9 pages).

* cited by examiner

*Primary Examiner* — Paul V Ward
(74) *Attorney, Agent, or Firm* — Merchant & Gould P.C.

(57) ABSTRACT

The invention is based on the finding that Airway Basal Cells (ABCs) play a key role in the pathobiology of various lung diseases. The invention therefore provides approaches for the treatment and prevention of lung diseases such as fibrotic disorders, pre stages of fibrosis, Chronic Obstructive Lung Diseases (COPD) or other lung disorders. Diseases treatable with the means and methods of the invention are characterized by a cellular remodelling in the alveolar compartment of the lung. Furthermore, the invention provides screening approaches to identify compounds suitable for the treatment of lung diseases.

12 Claims, 17 Drawing Sheets

FIGURE 7

| Y-27632 | ROCK inhibitor, calcium sensitizer, leucine rich repeat kinase inhibitor |
|---|---|
| PD-98059 | MEK inhibitor, MAP kinase inhibitor |
| tivozanib | VEGFR inhibitor, KIT inhibitor, tyrosine kinase inhibitor |
| PTB1 | AMPK activator, tyrosine phosphatase inhibitor |
| UNC-0321 | histone lyinse methyltransferase inhibitor, histone lysine methyltransferase inhibitor |
| tofacitinib | JAK inhibitor, disease modifying antirheumatic drug, immunosuppressant, MAP kinase inhibitor, tyrosine kinase inhibitor |
| phenazopyridine | unidentified pharmacological activity |
| selumetinib | MEK inhibitor, MAP kinase inhibitor |
| apigenin | casein kinase inhibitor, cell proliferation inhibitor, cytochrome P450 inhibitor, GABA receptor antagonist, glutamate receptor antagonist, monoamine oxidase inhibitor, nitric oxide production inhibitor, ornithine decarboxylase inhibitor, quorum sensing signaling modulator, VEGF expression inhibitor, xanthine oxidase inhibitor |
| erythrosine | food coloring agent |
| Cyclo-[Arg-Gly-Asp-D-Phe-Val] | integrin antagonist |
| fasudil | ROCK inhibitor, calcium sensitizer, PKA inhibitor, protein kinase inhibitor, rho associated kinase inhibitor |
| PP-2 | src inhibitor |
| SB-202190 | p38 MAPK inhibitor, interleukin inhibitor, stress activated protein kinase inhibitor |
| TWS-119 | glycogen synthase kinase inhibitor |
| 9-methyl-5H-6-thia-4,5-diaza- | NFkB pathway inhibitor |

FIGURE 7 cont.

| | |
|---|---|
| chrysene-6,6-dioxide | |
| fostamatinib | syk inhibitor, FLT3 inhibitor |
| EMF-bca1-50 | caspase inhibitor |
| dasatinib | KIT inhibitor, src inhibitor, Bcr-Abl kinase inhibitor, ephrin receptor inhibitor, PDGFR tyrosine kinase receptor inhibitor, yes kinase inhibitor, Abl kinase inhibitor, Bruton's tyrosine kinase (BTK) inhibitor, discoidin domain containing receptor inhibitor, lymphocyte specific tyrosine kinase inhibitor, tyrosine kinase inhibitor |
| CG-930 | JNK inhibitor |
| AZ-628 | RAF inhibitor |
| RG-13022 | EGFR inhibitor, PDGFR tyrosine kinase receptor inhibitor |
| sildenafil | phosphodiesterase inhibitor |
| FR-180204 | MAP kinase inhibitor |
| PD-0325901 | MEK inhibitor, MAP kinase inhibitor, protein kinase inhibitor |
| GSK-429286A | ROCK inhibitor |
| MEK1-2-inhibitor | MEK inhibitor |
| PP-1 | src inhibitor, Abl kinase inhibitor |
| tyrphostin-AG-112 | protein tyrosine kinase inhibitor |
| FTI-276 | farnesyltransferase inhibitor |
| tipifarnib | farnesyltransferase inhibitor, angiogenesis inhibitor, apoptosis stimulant |
| myriocin | sphingolipid biosynthesis inhibitor |
| AS-703026 | MEK inhibitor |
| TPCA-1 | IKK inhibitor |
| atorvastatin | HMGCR inhibitor, dipeptidyl peptidase inhibitor, tumor necrosis factor expression inhibitor |
| baeomycesic-acid | lipoxygenase inhibitor |
| LY-364947 | TGF beta receptor inhibitor, p38 MAPK inhibitor |
| xanthoxyline | plant-derived antifungal |
| fatostatin | sterol regulatory element binding protein (SREBP) inhibitor |
| PD-0325901 | MEK inhibitor, MAP kinase inhibitor, protein kinase inhibitor |
| RHO-kinase-inhibitor-III[rockout] | ROCK inhibitor |
| lovastatin | HMGCR inhibitor |
| BMS-536924 | insulin growth factor receptor inhibitor, insulin receptor ligand |
| PKCbeta-inhibitor | PKC inhibitor |
| PD-184352 | MEK inhibitor, MAP kinase inhibitor |
| PJ-34 | PARP inhibitor |
| simvastatin | HMGCR inhibitor |
| JAK3-inhibitor-I | JAK inhibitor |
| PCA-4248 | platelet activating factor receptor antagonist |
| KIN001-242 | protein kinase inhibitor |
| WH-4023 | src inhibitor |
| SIB-1757 | glutamate receptor antagonist |
| phenothiazine | dopamine receptor antagonist |
| AS-605240 | Phosphatidylinositol 3-kinase (PI3K) inhibitor, PI3K inhibitor |
| saracatinib | src inhibitor, Abl kinase inhibitor |
| U0126 | MEK inhibitor, JAK inhibitor, MAP kinase inhibitor |
| JZL-184 | monoacylglycerol lipase inhibitor |
| VER-155008 | HSP inhibitor |

FIGURE 7 cont.

| CP-724714 | receptor tyrosine protein kinase inhibitor, EGFR inhibitor, tyrosine kinase inhibitor |
|---|---|
| NVP-AUY922 | HSP inhibitor |
| U-0126 | MEK inhibitor, JAK inhibitor, MAP kinase inhibitor |
| forskolin | adenylyl cyclase activator, Adenylate cyclase stimulant, growth hormone receptor agonist, phosphokinase stimulant |
| AZD-7762 | CHK inhibitor |
| 17-hydroxyprogesterone-caproate | progesterone receptor agonist |
| purmorphamine | smoothened receptor agonist |
| HSP90-inhibitor | HSP inhibitor, HSP antagonist |
| daunorubicin | RNA synthesis inhibitor, topoisomerase inhibitor, DNA synthesis inhibitor, radical formation stimulant |
| DMBI | platelet-derived growth factor receptor (PDGFR) inhibitor, tyrosine kinase inhibitor, vascular endothelial growth factor receptor (VEGFR) inhibitor |
| SB-366791 | TRPV antagonist |
| QL-XI-92 | DDR1 inhibitor |
| imiquimod | interferon inducer, toll-like receptor agonist, immunostimulant |
| sulfinpyrazone | platelet aggregation inhibitor |
| sinensetin | cyclooxygenase inhibitor |
| BRD-K85853281 | radical formation stimulant, RNA synthesis inhibitor, topoisomerase inhibitor |
| evodiamine | ATPase inhibitor, TRPV agonist |
| doxorubicin | topoisomerase inhibitor, DNA intercalating drug |
| rosuvastatin | HMGCR inhibitor |
| forskolin | adenylyl cyclase activator, Adenylate cyclase stimulant, growth hormone receptor agonist, phosphokinase stimulant |
| GR-46611 | serotonin receptor agonist |
| geranylgeraniol | farnesyltransferase inhibitor |
| nifedipine | calcium channel blocker, L-type calcium channel blocker |
| BRD-K71726959 | CDK inhibitor |
| prima-1-met | thioredoxin inhibitor, TP53 activator |
| troglitazone | PPAR receptor agonist, insulin sensitizer, CCK ligand expression inhibitor, EGR1 expression enhancer, glycogen synthase kinase stimulant |
| brivanib | alcohol dehydrogenase inhibitor, FGFR inhibitor, fibroblast growth factor receptor (FGFR) inhibitor, vascular endothelial growth factor receptor (VEGFR) inhibitor, VEGFR inhibitor |
| KIN001-055 | EGFR inhibitor, JAK inhibitor, leukotriene synthesis inhibitor, mediator release inhibitor |

MODULATORS OF AIRWAY BASAL CELLS FOR THE TREATMENT OR PREVENTION OF LUNG DISEASES

FIELD OF THE INVENTION

The invention is based on the finding that Airway Basal Cells (ABCs) play a key role in the pathobiology of various lung diseases. The invention therefore provides approaches for the treatment and prevention of lung diseases such as fibrotic disorders, pre stages of fibrosis, Chronic Obstructive Lung Diseases (COPD) or other lung disorders. Diseases treatable with the means and methods of the invention are characterized by a cellular remodelling in the alveolar compartment of the lung. Furthermore, the invention provides screening approaches to identify compounds suitable for the treatment of lung diseases.

DESCRIPTION

Idiopathic pulmonary fibrosis (IPF) is a progressive disease with a lethal prognosis despite the introduction of new anti-fibrotic treatments. The histological pattern of IPF, usual interstitial pneumonia (UIP), is characterized by patchy and peripheral remodelling of the alveolar compartment with replacement of the normal alveolar architecture by fibroblastic foci, honeycomb cysts, and distorted airways. Recent data indicate that IPF exhibits features of small airway disease. Bronchiolization, the replacement of the resident alveolar epithelial cells by ABCs within remodeled regions in the IPF lung, leads to a dramatic shift in the epithelial cell repertoire of the alveolar compartment. The ABC is the progenitor cell of the airway epithelium and can give rise to any type of airway epithelial cell such as secretory, goblet or ciliated cells. ABCs play an important role in lung development, start the branching and tubing morphogenesis by building up the airway tree, and have been implicated in the pathogenesis of chronic obstructive pulmonary disease and lung cancer. It was recently confirmed the abundance of ABCs in the lung parenchyma of patients with IPF and discovered that the presence of an ABC signature in the transcriptome of bronchoalveolar lavage (BAL) cell pellet of patients was indicative of enhanced disease progression and mortality. However, it has not been clear whether ABCs contribute to the fibrotic process or simply represent a bystander phenomenon.

Although previous report indicated an association of ABCs with certain patho-biologic processes of fibrosis, no causal connection could be shown to date. Also, there is still no therapeutic option that tackles and prevents occurrence of lung diseases, in particular fibrosis, at stages where the disease has not yet manifested.

Thus, it is an objection of the invention to provide means and methods for the prevention and treatment of lung diseases such as pulmonary fibrosis.

BRIEF DESCRIPTION OF THE INVENTION

Generally, and by way of brief description, the main aspects of the present invention can be described as follows:

In a first aspect, the invention pertains to a compound for use in the treatment and/or prevention of a lung disease in a subject, wherein the lung disease is characterized by the presence of a pathological phenotype of Airway Basal Cells (ABCs) in the lung of the subject, and wherein the compound is an inhibitor of a pathway listed in table 1, or is an inhibitor listed in table 2, or a functional analogue thereof, preferably wherein the functional analogue is an inhibitor of another component of a cell biologic pathway targeted by any of the inhibitors listed in table 2. Alternatively, the first aspect pertains to a method for treatment of a lung disease in a subject, wherein the treatment comprises the administration of the compound in a therapeutically effective amount to the subject, and thereby treating the lung disease.

In a second aspect, the invention pertains to a method for the treatment and/or prevention of a lung disease in a subject, the method comprising the steps of administering to the subject a therapeutically and/or preventive amount of a compound recited in any one of the preceding claims.

In a second aspect, the invention pertains to a method for the treatment and/or prevention of a lung disease in a subject, the method comprising the steps of administering to the subject a therapeutically and/or preventive amount of a compound recited in any one of the preceding claims.

In a third aspect, the invention pertains to a method for identifying and/or characterizing a compound suitable for the treatment of a lung disease, the method comprising the steps of:
  Providing at least one ABC, optionally at least lung fibroblast, and a candidate compound;
  Bringing into contact the least one ABC, optionally the at least lung fibroblast, and the candidate compound;
  Detecting and/or quantifying any one or a combination of the following screening markers: (a) formation of bronchospheres, (b) ABC proliferation and/or ABC viability, (c) when lung firboblasts are used in (i) and (ii) fibroblast proliferation and/or collagen production;
wherein a differential level of at least one screening marker as detected and/or quantified in (iii) when the least one ABC, optionally the at least lung fibroblast, are contacted with the candidate compound compared to when the least one ABC, optionally the at least lung fibroblast, are not contacted with the candidate compound indicates the candidate compound as suitable for the treatment of the lung disease.

In a fourth aspect, the invention pertains to a method of reducing and/or inhibiting a cellular remodeling in the alveolar compartment of the lung of a subject in need of the treatment, the method comprising administering to the subject an effective amount of a compound recited herein, in particular in context of the disclosure of the first aspect.

DETAILED DESCRIPTION OF THE INVENTION

In the following, the elements of the invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine two or more of the explicitly described embodiments or which combine the one or more of the explicitly described embodiments with any number of the disclosed and/or preferred elements. Furthermore, any permutations and combinations of all described elements in this application should be considered disclosed by the description of the present application unless the context indicates otherwise.

In a first aspect, the invention pertains to a compound for use in the treatment and/or prevention of a lung disease in a subject, wherein the lung disease is characterized by the presence of a pathological phenotype of Airway Basal Cells (ABCs) in the lung of the subject, and wherein the compound is an inhibitor of a pathway listed in table 1, or is an inhibitor listed in table 2, or a functional analogue thereof, preferably wherein the functional analogue is an inhibitor of another component of a cell biologic pathway targeted by any of the inhibitors listed in table 2.

TABLE 1

Inhibitors potentially beneficial in ABC driven lung diseases:

MEK Inhibitor
SRC Inhibitor
C2 domain containing protein kinases
LOF
Rho associated kinase (ROCK) Inhibitor
PARP Inhibitor
GPCR Subset GOF
JAK 3 Inhibitor
HSP 90 Inhibitor
Topoisomerase II Inhibitor
HMGCR Inhibitor
Mediator complex LOF
PKA Inhibitor
IGF-1 Inhibitor
TGF beta receptor Inhibitor
VEGFR Inhibitor
P38 MAPK Inhibitor
S100 calcium binding proteins LOF
Integrin subunits beta LOF
Beta-adrenergic receptor Agonisten
Bromodomain Inhibitor
EGFR Inhibitor
RAF Inhibitor Table 2 is shown in FIG. 7.

In addition the following substances were identified according to their potential to modulate the gene expression of the pathogenic ABC phenotype identified herein. The mentioned compounds should modulate and reverse the pathogenic ABC phenotype.

The present invention is predicated upon the detection of a causal connection between a pathological phenotype of ABCs which is characterized by differential gene expression compared to healthy ABCs and an effect of such pathological phenotype ABCs in co-culture experiments with fibroblasts in accordance with the herein disclosed examples that shows an augmented bronchosphere formation as well as enhanced proliferation and extracellular matrix (ECM) deposition by fibroblasts. The differential gene expression is characterized by enhanced sternness, extra-cellular matrix (ECM) sensing and epidermal growth factor (EGF) signalling. Hence, in some embodiments the lung disease is characterized by a remodeling of lung alveolar or tissue.

In certain preferred embodiments the lung disease according to the invention is characterized by a presence of a pathological phenotype of Airway Basal Cells (ABCs) in the lung of the subject and wherein the lung disease is caused by said pathological phenotype of ABCs, for example, and in certain embodiments preferably, by their capacity to increase bronchosphere formation, lung fibroblast proliferation, formation of airway structures, formation of cystic structures, lung fibroblast collagen production, EGFR phosphorylation and/or alpha-smooth muscle (α-SMA) expression. In certain preferred embodiments such lung diseases may be further characterized by being a fibrotic disease, Chronic Obstructive Lung Disease (COPD) or asthma.

In some embodiments the pathological phenotype of ABCs in the subject comprises that the ABCs in the subject are involved in a lung remodeling, preferably a cellular remodeling in the alveolar compartment of the lung.

In some preferred embodiments, the treatment involves an inhibition of the interaction of ABCs as described herein with lung fibroblasts. Such interaction is preferably mediated by amphiregulin.

The term "lung fibrosis" refers to a group of fibrotic diseases or disorders affecting the lung, such as idiopathic pulmonary fibrosis (IPF), familial interstitial pulmonary fibrosis, nonspecific interstitial pneumonia (NSIP), cryptogenic organizing pneumonia (COP), sarcoidosis, chronic obstructive pulmonary disease (COPD), and asbestosis. "Fibrotic diseases or disorders affecting the lung" or "fibrotic lung disease or disorder" are terms which are used interchangeably herein and refer to a respiratory disease in which scars are formed due to the accumulation of excess fibrous connective tissue in the lung tissues, mainly collagen, leading to progressive loss of lung function. The accumulation of excess fibrous connective tissue leads to thickening of alveolar walls, leading to reduced lung function. As a consequence, patients suffer from shortness of breath, are unable to exert themselves physically, and are at risk for pneumonia or other serious lung infections. In some patients, the specific cause of the disease can be diagnosed, but in others the probable cause cannot be determined, a condition called idiopathic pulmonary fibrosis (IPF). There are no treatments to reverse fibrosis or prevent further loss of lung function.

The term "idiopathic pulmonary fibrosis (IPF)" refers to a disease of the lung that occurs in middle-aged and elderly adults (median age at diagnosis 66 years, range 55-75 years). IPF is limited to the lungs, and is associated with a histopathological or radiological pattern typical of usual interstitial pneumonia. The cause of IPF is unknown, however a history of smoking, genetic factors, and environmental insults are thought to trigger the pathological changes that lead to fibrotic remodeling of lung tissue. After lung injury, epithelial cells release inflammatory mediators that initiate an anti-fibrinolytic coagulation cascade, which triggers platelet activation and blood clot formation. This is followed by entry of leukocytes (e.g., neutrophils, macrophages, and T cells). The recruited leukocytes secrete pro-fibrotic cytokines such as IL-1 b, TNF-a, and TGF-b. In the subsequent phase, fibroblasts and myofibroblasts are derived from epithelial cells undergoing epithelial to mesenchymal transition, as well as fibrocytes from the bone marrow, and resident fibroblasts that proliferate and differentiate into myofibroblasts. These cells release collagen and other fibrotic components. IPF is a chronic, progressive, irreversible, and eventually lethal lung disease.

As used herein, the term "asthma" refers to a chronic condition, which in most cases is characterized by reversible airway obstructions and/or constrictions. The airway becomes inflamed and is lined with excessive amounts of mucus, often in response to one or more triggers for asthma. The triggers for asthma include, but are not limited to, an environmental stimulant, such as an allergen (ragweed, house dust, animal hair, pollen, etc.), cold air, warm air, moist air, change in temperature or humidity, upper respiratory infections, exercise, exertion, physical or emotional stress, smoke, viral illnesses such as those caused by common cold. The term "asthma" includes those caused by any cause of asthma whose primary effect is cellular inflammation and/or irritation, whether involving mast cells or not, degranulation or not, mucus exudation or not, whether exacerbant is identified or not, or whether the cause is airborne or not. The term 'asthma' is to be the widest-encompassing and is to include breathing difficulty of all degrees from the barely perceptible to acute.

Examples of asthma include, but are not limited to bronchial asthma, infantile asthma, allergic asthma, atopic asthma, steroid refractory asthma, non-allergic asthma, endogenous asthma, exogenous asthma, aspirin asthma, cardiac asthma, exercise-induced asthma, infectious asthma, any asthma triggered by airway restriction or constriction.

As used herein, the term "chronic obstructive pulmonary disease" or "COPD", also known as chronic obstructive airway disease (COAD), refers to a progressive respiratory disease characterized by limitation of airflow in the airway that is not fully reversible. COPD often involves permanent or temporary narrowing of small bronchi, in which forced expiratory flow is slowed. Examples of COPD include chronic bronchitis, emphysema and a range of other disorders to which no etiologic or other more specific term can be applied. COPD is most often due to tobacco smoking but can be due to other airborne irritants, such as coal dust, asbestos or solvents, as well as preserved meats containing nitrites.

In some further embodiments the lung disease is characterized by a remodelling of alveolar epithelial cells and/or tissue, and that has not yet developed into a lung fibrosis. Hence, in certain of such embodiments it is preferred that a subject of the invention is expected to develop a lung disease, but does not have the lung disease, preferably lung fibrosis, yet. This embodiment is based on the finding that the treatment of the invention in in-vivo experiments, such as a c-Src inhibitor treatment inhibits the development of a lung fibrosis by reduction of remodelling of the alveolar compartment of the lung—hence, a preventive use to avoid lung fibrosis in the first place. Therefore the compound according to the invention is used for a prevention of lung fibrosis, preferably wherein the subject is at risk of, or suspected to, developing a lung fibrosis.

According to the invention, the lung disease is characterized by an increased (pathological) expression and/or activity of c-Src in the lung of the subject, preferably wherein an increased expression and/or activity of c-Src in the subject is increased compared to the expression and/or activity of c-Src in a lung of a heathy subject.

In some preferred embodiments the compound of the invention is an inhibitor of c-Src signalling, and preferably is a c-Src inhibitor. As used herein, the term "SRC inhibitor" has its general meaning in the art and refers to any compound, natural or synthetic, that blocks, suppresses, or reduces the biological activity of SRC or to any compound that inhibits SRC gene expression.

The c-Src inhibitor may be at least one selected from the group consisting of dasatinib, saracatinib ((N-(5-chloro-1,3-benzodioxol-4-yl)-7-[2-(4-methyl-1-piperazinyl)ethoxy]-5-[(tetrahydro-2H-pyran-4-yl]oxy)-4-quinazolinamine; CAS No. 379231-04-6; also known as AZD-0530), bosutinib, 1-Naphthyl PP1 (CAS 221243-82-9; 1-(1,1-Dimethylethyl)-3-(1-naphthalenyl)-1H-pyrazolo[3,4-d]pyrimidin-4-amine), A 419259 trihydrochloride (CAS 364042-47-7; 7-[trans-4-(4-Methyl-1-piperazinyl)cyclohexyl]-5-(4-phenoxyphenyl)-7H-Pyrrolo[2,3-d]pyrimidin-4-amine trihydrochloride), AG 538 (CAS 133550-18-2; α-Cyano-(3,4-dihydroxy)cinnamoyl-(3',4'-dihydroxyphenyl)ketone), AGL 2263 ((E)-2-(3,4-dihydroxybenzoyl)-3-(2-oxo-3H-1,3-benzoxazol-5-yl)prop-2-enenitrile), Bcr-abl Inhibitor II (CAS 607702-99-8; 4-fluoro-N-{5-[(4-fluorobenzyl)sulfanyl]-1,3,4-thiadiazol-2-yl}benzamide), Bosutinib (CAS 380843-75-4; 4-[(2,4-Dichloro-5-methoxyphenyl)amino]-6-methoxy-7-[3-(4-methyl-1-piperazinyl)propoxy]-3-quinolinecarbonitrile), Altenusin (CAS 31186-12-6), Herbimycin A (CAS 70563-58-5; (15R)-17-demethoxy-15-methoxy-11-O-methyl-geldanamycin), PD 166285 (CAS 212391-63-4; 6-(2,6-Dichlorophenyl)-2-[[4-[2-(diethylamino)ethoxy]phenyl]amino]-8-methylpyrido[2,3-d]pyrimidin-7(8H)-one), PKC-412 (CAS 120685-11-2; [9S-(9α,10β,11β,13α]-N-(2,3,10,11,12,13-Hexahydro-10-methoxy-9-methyl-1-oxo-9,13-epoxy-1H,9H-diindolo[1,2,3-gh:3',2',1'-lm]pyrrolo[3,4-j][1, 7]benzodiazonin-11-yl)-N-methylbenzamide), PDGFR Tyrosine Kinase Inhibitor IV (CAS 627518-40-5; 3-Fluoro-N-(6,7-dimethoxy-2,4-dihydroindeno[1,2-c]pyrazol-3-yl)phenylamine), Calphostin C (CAS 121263-19-2; (1R)-2-[12-[(2R)-2-(Benzoyloxy)propyl]-3,10-dihydro-4,9-dihydroxy-2,6,7,11-tetramethoxy-3,10-dioxo-1-perylenyl]-1-methylethylcarbonic acid 4-hydroxyphenyl ester), PP 1 (CAS 172889-26-8; 1-tert-butyl-3-(4-methylphenyl) pyrazolo[3,4-d]pyrimidin-4-amine), PP 2 (CAS 172889-27-9; 4-Amino-5-(4-chlorophenyl)-7-(t-butyl)pyrazolo[3,4-d]pyrimidine), Src Kinase Inhibitor I (CAS 179248-59-0; 4-(4'-Phenoxyanilino)-6,7-dimethoxyquinazoline), EGF/FGF/PDGF Receptor Tyrosine Kinase Inhibitor (CAS 1135256-66-4; 1-(2-Amino-6-(2,6-dichlorophenyl)pyrido[2,3-d]pyrimidin-7-yl)-3-tert-butyl urea), Staurosporine (CAS 62996-74-1; [9S-(9α,10β,11β,13α]-2,3,10,11,12,13-Hexahydro-1-methoxy-9-methyl-11-(methylamino)-9,13-epoxy-1H,9H-diindolo[1,2,3-gh:3',2',1'-lm]pyrrolo[3,4-j][1,7]benzodiazonin-1-one), Lavendustin A (CAS 125697-92-9; 5-[[(2,5-Dihydroxyphenyl)methyl][(2-hydroxyphenyl)methyl]amino]-2-hydroxybenzoic acid), Indirubin-3'-(2,3-dihydroxypropyl)oximether, Luteolin (CAS 491-70-3; 2-(3,4-Dihydroxyphenyl)-5,7-dihydroxy-4H-1-benzopyran-4-one), SU6656 (CAS 330161-87-0; (3Z)—N,N-Dimethyl-2-oxo-3-(4,5,6,7-tetrahydro-1H-indol-2-ylmethylidene)-2,3-dihydro-1H-indole-5-sulfonamide), TX-1918 (CAS 503473-32-3; 2-((3,5-dimethyl-4-hydroxyphenyl)-methylene)-4-cyclopentene-1,3-dione), Geldanamycin (CAS 30562-34-6; 2-azabicyclo[16.3.1]docasa-4,6,10,18,21-pentaene-3,20,22-trione, 9,13-dihydroxy-8,14,19-trimethoxy-4,10,12,16-tetramethyl-9-carbamate), MNS (CAS 1485-00-3; 3,4-Methylenedioxy-nitrostyrene), TX-1123 (CAS 157397-06-3; 2-((3,5-di-tert-Butyl-4-hydroxyphenyl)-methylene)-4-cyclopentene-1,3-dione), GW5074 (CAS 220904-83-6; 3-(3,5-Dibromo-4-hydroxybenzylidene)-5-iodo-1,3-dihydro-indol-2-one), Erlotinib HCl (CAS 183319-69-9; N-(3-ethynylphenyl)-6,7-bis(2-methoxyethoxy)quinazolin-4-amine hydrochloride), NVP-BHG712 (CAS 940310-85-0; 4-methyl-3-(1-methyl-6-(pyridin-3-yl)-1H-pyrazolo[3,4-d]pyrimidin-4-ylamino)-N-(3-(trifluoromethyl)phenyl)benzamide), GW2580 (CAS 870483-87-7; 5-[[3-methoxy-4-[(4-methoxyphenyl)methoxy]phenyl]methyl]-2,4-Pyrimidinediamine), AEE788 (CAS 497839-62-0; (R)-6-(4-((4-ethylpiperazin-1-yl)methyl)phenyl)-N-(1-phenylethyl)-7H-pyrrolo[2,3-d]pyrimidin-4-amine), TAK-901 (CAS 934541-31-8; 5-(3-(ethylsulfonyl)phenyl)-3,8-dimethyl-N-(1-methylpiperidin-4-yl)-9H-pyrido[2,3-b]indole-7-carboxamide), Midostaurin (CAS 120685-11-2; N-[(9S,10R,11R,13R)-2,3,10,11,12,13-hexahydro-10-methoxy-9-methyl-1-oxo-9,13-epoxy-1H,9H-diindolo[1,2,3-gh:3',2',1'-lm]pyrrolo[3,4-j][1,7]benzodiazonin-11-yl]-N-methylbenzamide), and PD173074 (CAS 219580-11-7; 1-tert-butyl-3-(2-(4-(diethylamino)butylamino)-6-(3,5-dimethoxyphenyl)pyrido[2,3-d]pyrimidin-7-yl)urea), or any combination thereof, but not be limited thereto.

A preferred c-Src inhibitor is bosutinib, saracatinib, danusertib, VP-BHG712, quercetin, PCI-32765, KX2-391, AP23451 or dasatinib.

Independently from the above in certain preferred embodiments the c-Src inhibitor is not saracatinib, preferably the compound is a c-Src-inhibitor other than saracatinib, such as bosutinib, danusertib, VP-BHG712, quercetin, PCI-32765, KX2-391, AP23451 or dasatinib.

A subject according to the invention is preferably a human, suitably an adult human. For example, a human that is 18 (or 16) years or older, such as a human between the ages of about 18 (or 16) and 90, or between 18 (or 16) and 80. In certain of such embodiments, the adult human is about 20 or older, 30 or older, 35 or older, 40 or older, 45 or older, 50 or older or 55 or older. In more particular of such embodiments, the adult human is a young adult (such as between about 18 (or 16) and 45 (or 40), or between about 30 and 45 (or 40)), is middle aged (such as between about 45 (or 40) and 65 (or 60), or between about 45 (or 40)) and 55 (or 50), or between about 55 (or 50) and 65 (or 60), or is elderly (such as being between about 60 and 90 (or older, such as 92, 95 or 98), between about 65 and 85 or between about 70 and 88).

A subject most preferably is a human adult older than 10 years, more preferably older than 20 years, more preferably is a subject between 20 and 90 years (or older), more preferably between 30 and 90 years (or older). Most preferably such a subject who is an adult human is at danger of developing a lung disease, such a subject has an age of 30 to 80. Such age ranges are particular preferred because the methods of the invention allow a prevention of the development of lung diseases at early stages.

A subject of the invention in additional or alternative embodiments is characterized by one or more of the following risk factors:
 The subject is or was a smoker;
 The subject suffers from gastroesophageal reflux;
 The subject received or receives antidepressant drugs, such as imipramine, dothiepin, or mianserin;
 The subject suffers from diabetes mellitus;
 The subject was or is exposed to metal or wood dust environments;
 The subject suffers from a viral disease, such as Eppstein Barr Virus, herpes simplex, influenza, measles, HIV, etc.

In a second aspect, the invention pertains to a method for the treatment and/or prevention of a lung disease in a subject, the method comprising the steps of administering to the subject a therapeutically and/or preventive amount of a compound recited in any one of the preceding claims.

In a third aspect, the invention pertains to a method for identifying and/or characterizing a compound suitable for the treatment of a lung disease, the method comprising the steps of:
 Providing at least one ABC, optionally at least lung fibroblast, and a candidate compound;
 Bringing into contact the least one ABC, optionally the at least lung fibroblast, and the candidate compound;
 Detecting and/or quantifying any one or a combination of the following screening markers: (a) formation of bronchospheres, (b) ABC proliferation and/or ABC viability, (c) when lung firboblasts are used in (i) and (ii) fibroblast proliferation and/or collagen production;
wherein a differential level of at least one screening marker as detected and/or quantified in (iii) when the least one ABC, optionally the at least lung fibroblast, are contacted with the candidate compound compared to when the least one ABC, optionally the at least lung fibroblast, are not contacted with the candidate compound indicates the candidate compound as suitable for the treatment of the lung disease.

A candidate compound preferably is a c-Src inhibitor, in some embodiments preferably not saracatinib.

In context of the invention any of the ABC model systems in the herein disclosed example section may be used. In this regards step (ii) may be performed in a 3D cell culture system.

Preferably the ABC and/or fibroblast are derived from a patient suffering from the lung disease, preferably fibrosis or a pre-stage of lung fibrosis.

In a fourth aspect, the invention pertains to a method of reducing and/or inhibiting a cellular remodeling in the alveolar compartment of the lung of a subject in need of the treatment, the method comprising administering to the subject an effective amount of a compound recited herein, in particular in context of the disclosure of the first aspect.

Generally administration of the compounds of the invention may be performed by any methods and routes known in the art. In some embodiments, in the event the compound used is saracatinib, the amount of saracatinib administered to an subject (e.g., via a composition or a pharmaceutical composition) can be, but is not limited to about 0.005 mg/kg, about 0.01 mg/kg, about 0.05 mg/kg, about 0.1 mg/kg, about 0.5 mg/kg, about 0.6 mg/kg, about 0.7 mg/kg, about 0.8 mg/kg, about 0.9 mg/kg, about 1.0 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2.0 mg/kg, about 2.1 mg/kg, about 2.2 mg/kg, about 2.3 mg/kg, about 2.4 mg/kg, about 2.5 mg/kg, about 2.6 mg/kg, about 2.7 mg/kg, about 2.8 mg/kg, about 2.9 mg/kg, about 3.0 mg/kg, about 3.1 mg/kg, about 3.2 mg/kg, about 3.3 mg/kg, about 3.4 mg/kg, about 3.5 mg/kg, about 3.6 mg/kg, about 3.7 mg/kg, about 3.8 mg/kg, about 3.9 mg/kg, about 4.0 mg/kg, about 4.1 mg/kg, about 4.2 mg/kg, about 4.3 mg/kg, about 4.4 mg/kg, about 4.5 mg/kg, about 5.0 mg/kg, about 5.5 mg/kg, about 6.0 mg/kg, about 6.5 mg/kg, about 7.0 mg/kg, about 7.5 mg/kg, about 10 mg/kg, about 20 mg/kg, about 30 mg/kg, about 40 mg/kg, about 50 mg/kg, about 80 mg/kg, about 100 mg/kg, about 150 mg/kg, no more than about 5.0 mg/kg, no more than about 4.5 mg/kg, no more than about 4.4 mg/kg, no more than about 4.3 mg/kg, no more than about 4.2 mg/kg, no more than about 4.1 mg/kg, no more than about 4.0 mg/kg, no more than about 3.9 mg/kg, no more than about 3.8 mg/kg, no more than about 3.7 mg/kg, no more than about 3.6 mg/kg, no more than about 3.5 mg/kg, no more than about 3.4 mg/kg, no more than about 3.3 mg/kg, no more than about 3.2 mg/kg, no more than about 3.1 mg/kg, no more than about 3.0 mg/kg, no more than about 2.9 mg/kg, no more than about 2.8 mg/kg, no more than about 2.7 mg/kg, no more than about 2.6 mg/kg, no more than about 2.5 mg/kg, no more than about 2.4 mg/kg, no more than about 2.3 mg/kg, no more than about 2.2 mg/kg, no more than about 2.1 mg/kg, no more than about 2.0 mg/kg, no more than about 1.9 mg/kg, no more than about 1.8 mg/kg, no more than about 1.7 mg/kg, no more than about 1.6 mg/kg, no more than about 1.5 mg/kg, no more than about 1.4 mg/kg, no more than about 1.3 mg/kg, no more than about 1.2 mg/kg, no more than about 1.1 mg/kg, no more than about 1.0 mg/kg, no more than about 0.9 mg/kg, no more than about 0.8 mg/kg, no more than about 0.7 mg/kg, no more than about 0.6 mg/kg, or no more than about 0.5 mg/kg animal body weight. The animal (e.g., human) body weight can be about 2 kg, about 5 kg, about 10 kg, about 15 kg, about 20 kg, about 25 kg, about 30 kg, about 35 kg, about 40 kg, about 45 kg, about 50 kg, about 55 kg, about 60 kg, about 65 kg, about 70 kg, about 75 kg, about 80 kg, about 85 kg, about 90 kg, about 95 kg, about 100 kg, about 150 kg, about 200 kg, from about 2 kg to about 200 kg, from about 10 kg to about 100 kg, from about 10 kg to about 85 kg, from about 45 kg to about 100 kg, or from about 45 kg to about 85 kg. These amounts (e.g., dosages) can be used as an effective amount or a therapeutically effective amount.

The route of administration for treatment can be of any suitable route. Administration routes can be, but are not limited to the oral route, the parenteral route, the cutaneous route, the nasal route, the rectal route, the vaginal route, and the ocular route. In other embodiments, the administration route can be parenteral administration, a mucosal administration, intravenous administration, depot injection, subcutaneous administration, topical administration, intradermal administration, oral administration, sublingual administration, intranasal administration, or intramuscular administration. In some embodiments, the administration can be an intranasal administration, an aerosol administration, a nebulizer administration, a pressurized metered-dose inhaler (pMDI) administration, an inhaler administration, or a dry powder inhaler (DPI) administration. The choice of administration route can depend on the compound identity (e.g., the physical and chemical properties of the compound) as well as the age and weight of the animal, the particular disease (e.g., the type of cystic fibrosis), and the severity of the disease (e.g., stage or severity of disease). Of course, combinations of administration routes can be administered, as desired.

In some embodiments, saracatinib, or another herein disclosed compound, can be part of a pharmaceutical composition and can be in an amount of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, no more than about 99.99%, from about 0.001% to about 99%, from about 0.001% to about 50%, from about 0.1% to about 99%, from about 1% to about 95%, from about 10% to about 90%, or from about 25% to about 75%. In some embodiments, the pharmaceutical composition can be presented in a dosage form which is suitable for the topical, subcutaneous, intrathecal, intraperitoneal, oral, parenteral, rectal, cutaneous, nasal, vaginal, or ocular administration route. In other embodiments, the pharmaceutical composition can be presented in a dosage form which is suitable for parenteral administration, a mucosal administration, intravenous administration, depot injection (e.g., solid or oil based), subcutaneous administration, topical administration, intradermal administration, oral administration, sublingual administration, intranasal administration, or intramuscular administration. In other embodiments, the pharmaceutical composition can be presented in a dosage form which is suitable for an intranasal administration, an aerosol administration, a nebulizer administration, a pressurized metered-dose inhaler (pMDI) administration, an inhaler administration, or a dry powder inhaler (DPI) administration. The pharmaceutical composition can be in the form of, for example, tablets, capsules, pills, powders granulates, suspensions, emulsions, solutions, gels (including hydrogels), pastes, ointments, creams, plasters, drenches, delivery devices, suppositories, enemas, injectables, implants, sprays, aerosols or other suitable forms.

In some embodiments, the pharmaceutical composition can include one or more formulary ingredients. A "formulary ingredient" can be any suitable ingredient (e.g., suitable for the drug(s), for the dosage of the drug(s), for the timing of release of the drugs(s), for the disease, for the disease state, or for the delivery route) including, but not limited to, water (e.g., boiled water, distilled water, filtered water, pyrogen-free water, or water with chloroform), sugar (e.g., sucrose, glucose, mannitol, sorbitol, xylitol, or syrups made therefrom), ethanol, glycerol, glycols (e.g., propylene glycol), acetone, ethers, DMSO, surfactants (e.g., anionic surfactants, cationic surfactants, zwitterionic surfactants, or nonionic surfactants (e.g., polysorbates)), oils (e.g., animal oils, plant oils (e.g., coconut oil or *arachis* oil), or mineral oils), oil derivatives (e.g., ethyl oleate, glyceryl monostearate, or hydrogenated glycerides), excipients, preservatives (e.g., cysteine, methionine, antioxidants (e.g., vitamins (e.g., A, E, or C), selenium, retinyl palmitate, sodium citrate, citric acid, chloroform, or parabens, (e.g., methyl paraben or propyl paraben)), or combinations thereof. For example, an intranasal administration, an aerosol administration, a nebulizer administration, a pressurized metered-dose inhaler (pMDI) administration, an inhaler administration, or a dry powder inhaler (DPI) administration, could include one or more formulary ingredients.

The terms "of the [present] invention", "in accordance with the invention", "according to the invention" and the like, as used herein are intended to refer to all aspects and embodiments of the invention described and/or claimed herein.

Further the invention is defined by the following itemized embodiments:

Item 1: A compound for use in the treatment and/or prevention of a lung disease in a subject, wherein the lung disease is characterized by the presence of a pathological phenotype of Airway Basal Cells (ABCs) in the lung of the subject, and wherein the compound is an inhibitor of a pathway listed in table 1, or is an inhibitor listed in table 2, or a functional analogue thereof, preferably wherein the functional analogue is an inhibitor of another component of a cell biologic pathway targeted by any of the inhibitors listed in table 2 (FIG. 7).

Item 2: The compound for use of item 1, wherein the pathological phenotype of ABCs in the subject comprises that the ABCs in the subject are involved in a lung remodelling, preferably cellular remodelling in the alveolar compartment of the lung.

Item 3: The compound for use of item 1, wherein the lung disease is characterized by a remodelling of alveolar epithelial cells and/or tissue, and that has not yet developed into a lung fibrosis.

Item 4: The compound for use of item 3, wherein the compound is used for a prevention of lung fibrosis, preferably wherein the subject is at risk of, or suspected to, developing a lung fibrosis but has not yet developed clinical signs of lung fibrosis.

Item 5: The compound for use of any one of items 1 to 4, wherein the lung disease is characterized by an increased (pathological) expression and/or activity of c-Src in the lung of the subject, preferably wherein an increased expression and/or activity of c-Src in the subject is increased compared to the expression and/or activity of c-Src in a lung of a heathy subject.

Item 6: The compound for use of any one of items 1 to 5, wherein the compound is an inhibitor of c-Src signalling, and preferably is a c-Src inhibitor.

Item 7: The compound for use of item 6, wherein the c-Src inhibitor is bosutinib, saracatinib, danusertib, VP-BHG712, quercetin, PCI-32765, KX2-391, AP23451 or dasatinib.

Item 8: The compound for use any one of items 1 to 6, which is not saracatinib, preferably wherein the compound is a Src-inhibitor other than saracatinib, such as bosutinib, danusertib, VP-BHG712, quercetin, PCI-32765, KX2-391, AP23451 or dasatinib.

Item 9: The compound for use of any one of items 1 to 8, wherein the subject is characterized by one or more of the following risk factors:
(i) The subject is or was a smoker;
(ii) The subject suffers from gastroesophageal reflux;
(iii) The subject received or receives antidepressant drugs, such as imipramine, dothiepin, or mianserin;
(iv) The subject suffers from diabetes mellitus;
(v) The subject was or is exposed to metal or wood dust environments;
(vi) The subject suffers from a viral disease, such as Eppstein Barr Virus, herpes simplex, influenza, measles, HIV, etc.

Item 10: A method for identifying and/or characterizing a compound suitable for the treatment of a lung disease, the method comprising the steps of:
(i) Providing at least one ABC, optionally at least lung fibroblast, and a candidate compound;
(ii) Bringing into contact the least one ABC, optionally the at least lung fibroblast, and the candidate compound;
(iii) Detecting and/or quantifying any one or a combination of the following screening markers: (a) formation of bronchospheres, (b) ABC proliferation and/or ABC viability, (c) when lung firboblasts are used in (i) and (ii) fibroblast proliferation and/or collagen production;
wherein a differential level of at least one screening marker as detected and/or quantified in (iii) when the least one ABC, optionally the at least lung fibroblast, are contacted with the candidate compound compared to when the least one ABC, optionally the at least lung fibroblast, are not contacted with the candidate compound indicates the candidate compound as suitable for the treatment of the lung disease.

Item 11: The method of item 10, wherein the candidate compound is an c-Src inhibitor, preferably not saracatinib.

Item 12: The method of any one of items 10 to 11, wherein the ABC and/or fibroblast are derived from a patient suffering from the lung disease, preferably fibrosis or a pre-stage of lung fibrosis.

Item 13: The method of any one of items 10 to 12, wherein the lung disease is a disease recited in any one of items 1 to 9.

As used herein, the term "comprising" is to be construed as encompassing both "including" and "consisting of", both meanings being specifically intended, and hence individually disclosed embodiments in accordance with the present invention. Where used herein, "and/or" is to be taken as specific disclosure of each of the two specified features or components with or without the other. For example, "A and/or B" is to be taken as specific disclosure of each of (i) A, (ii) B and (iii) A and B, just as if each is set out individually herein. In the context of the present invention, the terms "about" and "approximately" denote an interval of accuracy that the person skilled in the art will understand to still ensure the technical effect of the feature in question. The term typically indicates deviation from the indicated numerical value by ±20%, ±15%, ±10%, and for example ±5%. As will be appreciated by the person of ordinary skill, the specific such deviation for a numerical value for a given technical effect will depend on the nature of the technical effect. For example, a natural or biological technical effect may generally have a larger such deviation than one for a man-made or engineering technical effect. As will be appreciated by the person of ordinary skill, the specific such deviation for a numerical value for a given technical effect will depend on the nature of the technical effect. For example, a natural or biological technical effect may generally have a larger such deviation than one for a man-made or engineering technical effect. Where an indefinite or definite article is used when referring to a singular noun, e.g. "a", "an" or "the", this includes a plural of that noun unless something else is specifically stated.

It is to be understood that application of the teachings of the present invention to a specific problem or environment, and the inclusion of variations of the present invention or additional features thereto (such as further aspects and embodiments), will be within the capabilities of one having ordinary skill in the art in light of the teachings contained herein.

Unless context dictates otherwise, the descriptions and definitions of the features set out above are not limited to any particular aspect or embodiment of the invention and apply equally to all aspects and embodiments which are described.

All references, patents, and publications cited herein are hereby incorporated by reference in their entirety.

BRIEF DESCRIPTION OF THE FIGURES

The figures show:

FIG. 7: shows a list of candidate compounds and pathways that could therapeutically modulate the ABC phenotype.

EXAMPLES

Certain aspects and embodiments of the invention will now be illustrated by way of example and with reference to the description, figures and tables set out herein. Such examples of the methods, uses and other aspects of the present invention are representative only, and should not be taken to limit the scope of the present invention to only such representative examples.

Figure 1:
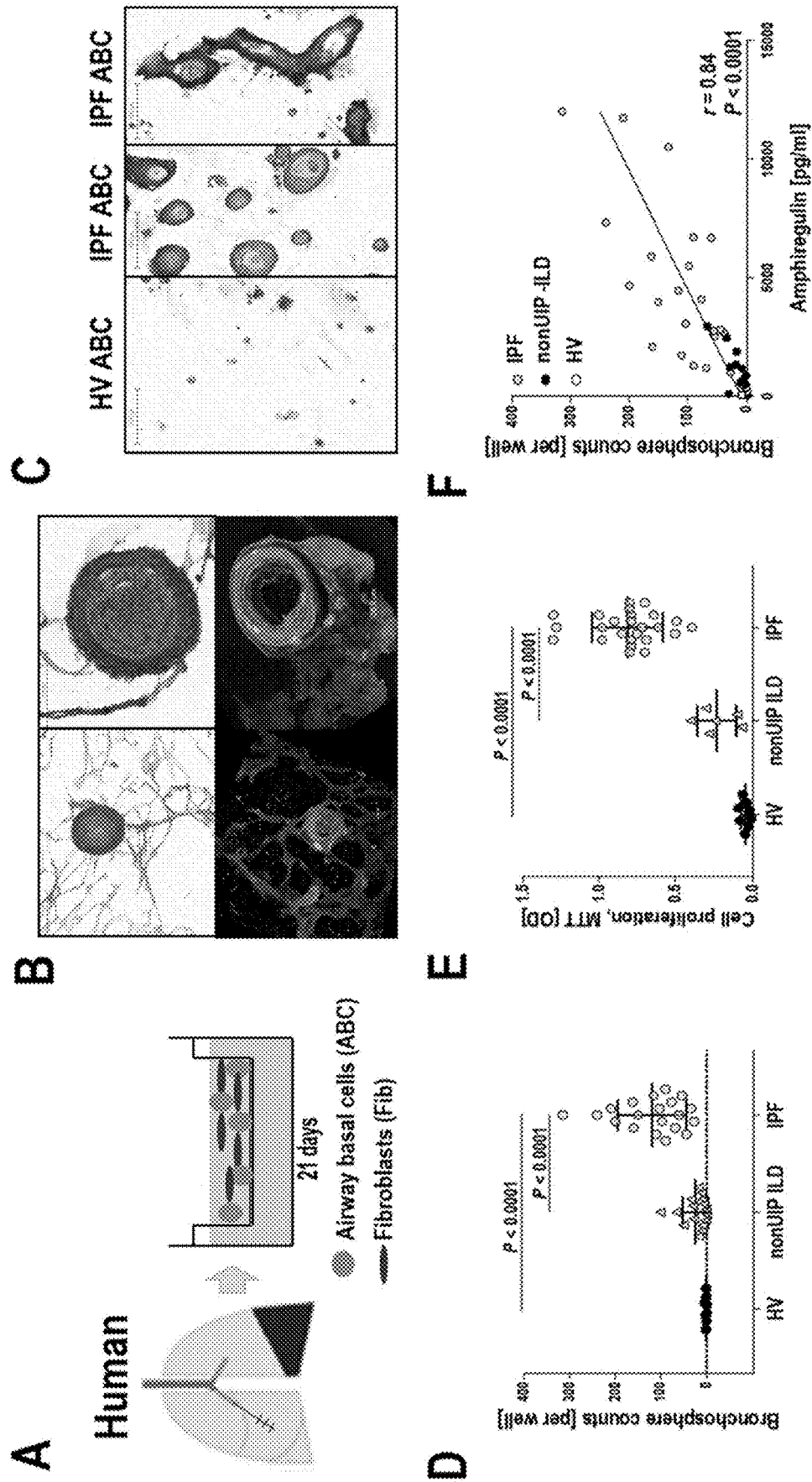
FIG. 1: IPF-ABCs generate more bronchospheres and increase fibroblast proliferation and collagen production compared to non-IPF cells in a 3D organoid model. (A) Airway basal cells w/wo human lung fibroblasts were cultured in matrigel applying a transwell system. (B) IPF-ABCs form large spheres which become hollow tube-like structures after 21 days of 3D culture. In the co-culture system of ABCs with lung fibroblasts, fibroblasts surround bronchospheres and form a mesh-like structure. Upper panel: Masson trichrome staining, scale bars 100 μm or 200 μm as indicated. Lower panel: Confocal immunohistochemistry demonstrates tube formation by IPF-ABCs and close interaction with lung fibroblasts (red=vimentin, yellow=CK5/6, blue=TO-PRO-3=nuclei, n=10, scale bar 10 μm and 20 μm). (C) Immunohistochemisty of evolving bronchospheres stained for CK5/6 in red, p40 in turquoise and beta6 integrin in brown (n=9, scale bars 200 μm). (D) IPF-ABCs (n=23) generated significantly more and larger spheres than HV-ABCs (n=7; P<0.0001) and NU-ABCs (n=15, P<0.0001). (E) Cell proliferation was also significantly increased in IPF-ABCs (n=23) compared to HV-ABCs (n=7, P<0.0001) and NU-ABCs (n=6, P<0.0001) as measured by MTT assay at d21. (F) Amphiregulin levels were increased in conditioned medium of bronchospheres from IPF-ABCs (n=23) compared to HV-ABCs (n=7) and NU-ABCs (n=15) and correlated closely with bronchosphere counts. (G) Bright field images of raster microscopy of an original experiment (10 independent experiments in triplicate). Lung fibroblasts do not form spheres. Sphere formation by IPF-ABCs is easily detectable. (H) In the presence of lung fibroblasts (n=5 IPF-Fib, n=5 HV-Fib), IPF-ABCs and HV-ABCs generate increased numbers of bronchospheres. (I) Fibroblast cell lines were transduced with lentiviral vectors encoding GFP. Fibroblast proliferation was highly increased in the presence of IPF-ABCs. (J) Mean fluorescence intensity was significantly increased in fibroblast cell lines co-cultured with IPF-ABCs (n=5). (K) Collagen levels were detected in conditioned medium and matrigel by sircol assay at day 63. Collagen production by lung fibroblasts cultured with IPF-ABCs was significantly increased (n=5). (L) In addition, fibroblasts cultured in conditioned medium of IPF-ABC derived bronchospheres (high BS) showed an increase in collagen 1A and α-smooth muscle actin (SMA) expression compared to conditioned medium of bronchosphere cultures derived from NU-ABCs (Low BS). (M) Lung fibroblasts were treated for 2 h with conditioned media of bronchospheres which were harvested at day 14. Pooled conditioned media of bronchospheres derived from IPF-ABCs (High BS) resulted in EGFR phosphorylation compared to conditioned media of bronchospheres derived from NU-ABCs (Low BS). For statistical comparison (D, E) ANOVA with Tukey correction for multiple testing, (F) Pearson correlation, (H, J, K) repeated measures ANOVA with Tukey correction for multiple testing was used.
Figure 1:
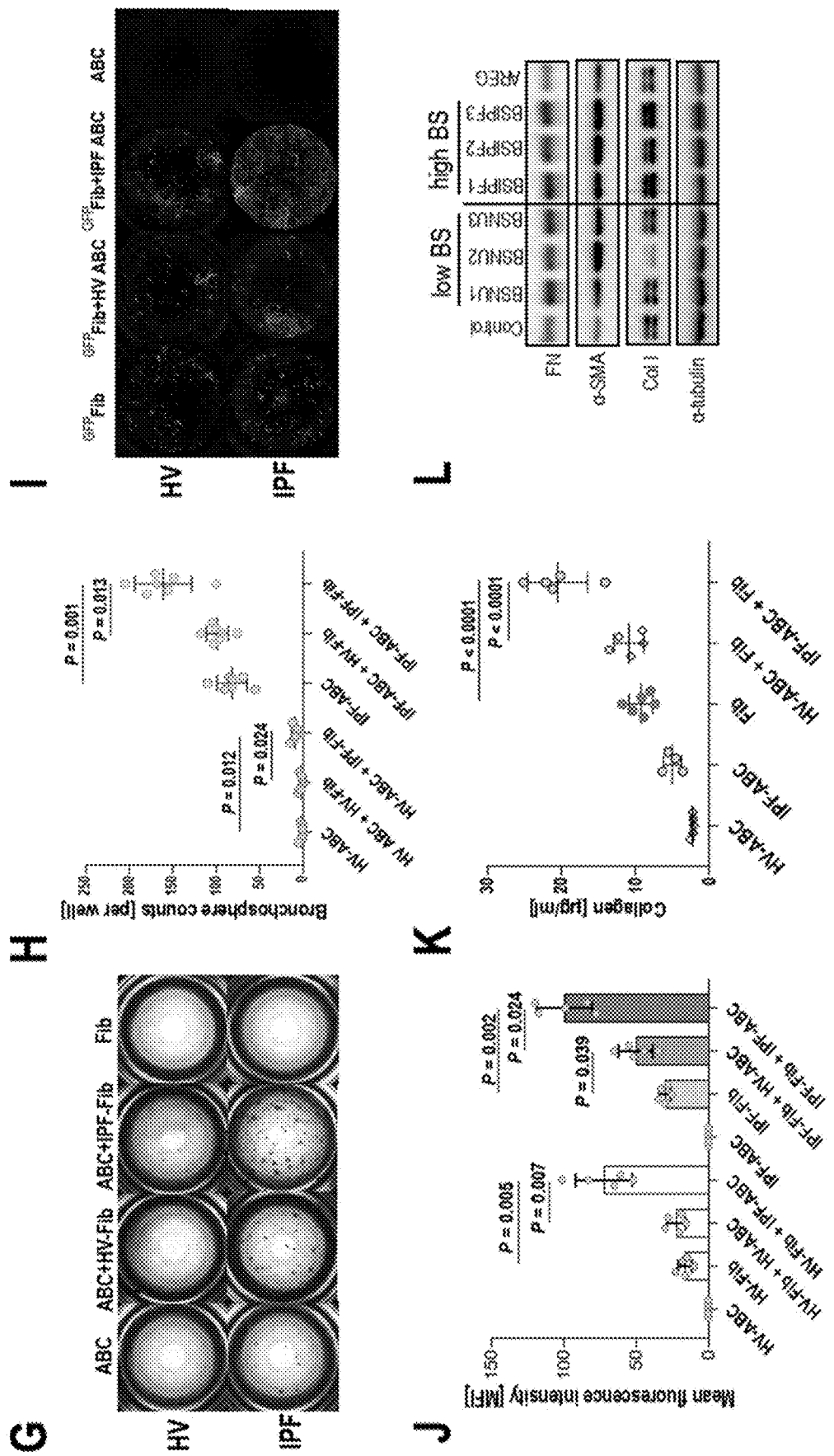
Figure 1:
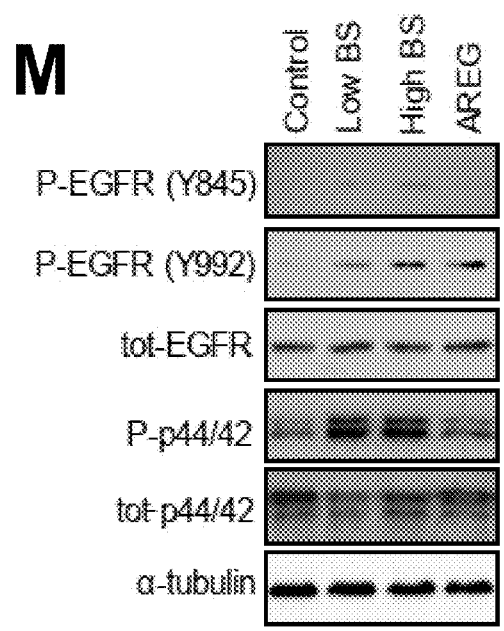

The examples show:

Example 1: ABCs from IPF Patients Generate Significantly More Bronchospheres than ABCs from Healthy Volunteers or nonUIP Interstitial Lung Disease (ILD) Patients in a 3D Organoid Model The inventors compared the bronchosphere formative capacity of ABCs from patients with IPF (IPF-ABC) to those obtained from healthy volunteers (HV-ABC) or individuals with fibrotic nonUIP ILD (NU-ABC) by plating the cells in 3D culture for 21 days (FIG. 1A-D). After 21 days, all three cell types formed organoids in 3D culture; however IPF-ABC formed organoids that were multilayered and frequently contain hollow and tube-like structures, visually resembling bronchospheres (FIGS. 1B and C). The average number of spheres per well generated by IPF-ABCs was significantly higher compared to HV-ABCs or NU-ABCs (120±73, 24±26 or, 2±2, respectively; P<0.0001, FIG. 1D). In addition, cell proliferation as measured at day 21 by MTT assay was also highly increased in IPF-ABCs compared to HV-ABCs and NU-ABCs (P<0.0001, FIG. 1E). Based on previously published data it was tested whether EGFR ligand production was up-regulated in IPF-ABCs. Indeed, conditioned medium of 3D organoid cultures of IPF-ABCs showed higher levels of amphiregulin (AREG) than HV-ABCs or NU-ABCs (P<0.0001), whereas HBEGF or TGF-$\beta$ were not detectable. Bronchosphere counts correlated with amphiregulin levels at day 14 (P<0.0001, r2=0.69, FIG. 1F).

Example 2: Presence of Fibroblasts Increased Bronchosphere Formation and IPF-ABCs Stimulated Fibroblast Proliferation and Collagen Production To assess the interaction of fibroblasts and ABCs the inventors added primary lung fibroblasts to our 3D cell culture system. IPF-ABCs formed bronchospheres similar to the ones observed before, which were now surrounded by a mesh of fibroblasts (FIG. 1B). Presence of lung fibroblasts in the 3D cell culture system, particularly primary cells derived from IPF explants, significantly enhanced bronchosphere formation of ABCs (P=0.012 and P=0.001, FIGS. 1G and H). Using GFP-transduced fibroblasts, we found that the overall fluorescence was significantly increased by IPF-ABCs in healthy (HV-Fib) as well as IPF fibroblasts (IPF-Fib), (P=0.005 and P=0.002 respectively, FIGS. 1I and J), potentially reflecting enhanced proliferation. IPF-ABCs significantly increased collagen production by lung fibroblasts compared to HV-ABCs (P<0.0001, FIG. 1K). Stimulation of lung fibroblasts with conditioned medium obtained from NU-ABC or IPF-ABC harvested at day 14 induced collagen and alpha-smooth muscle ($\alpha$-SMA) expression in lung fibroblasts (FIG. 1L) as well as induced EGFR phosphorylation (FIG. 1M), a finding consistent with significantly increased secretion of amphiregulin by IPF-ABC bronchospheres (FIG. 1F).

Figure 2:
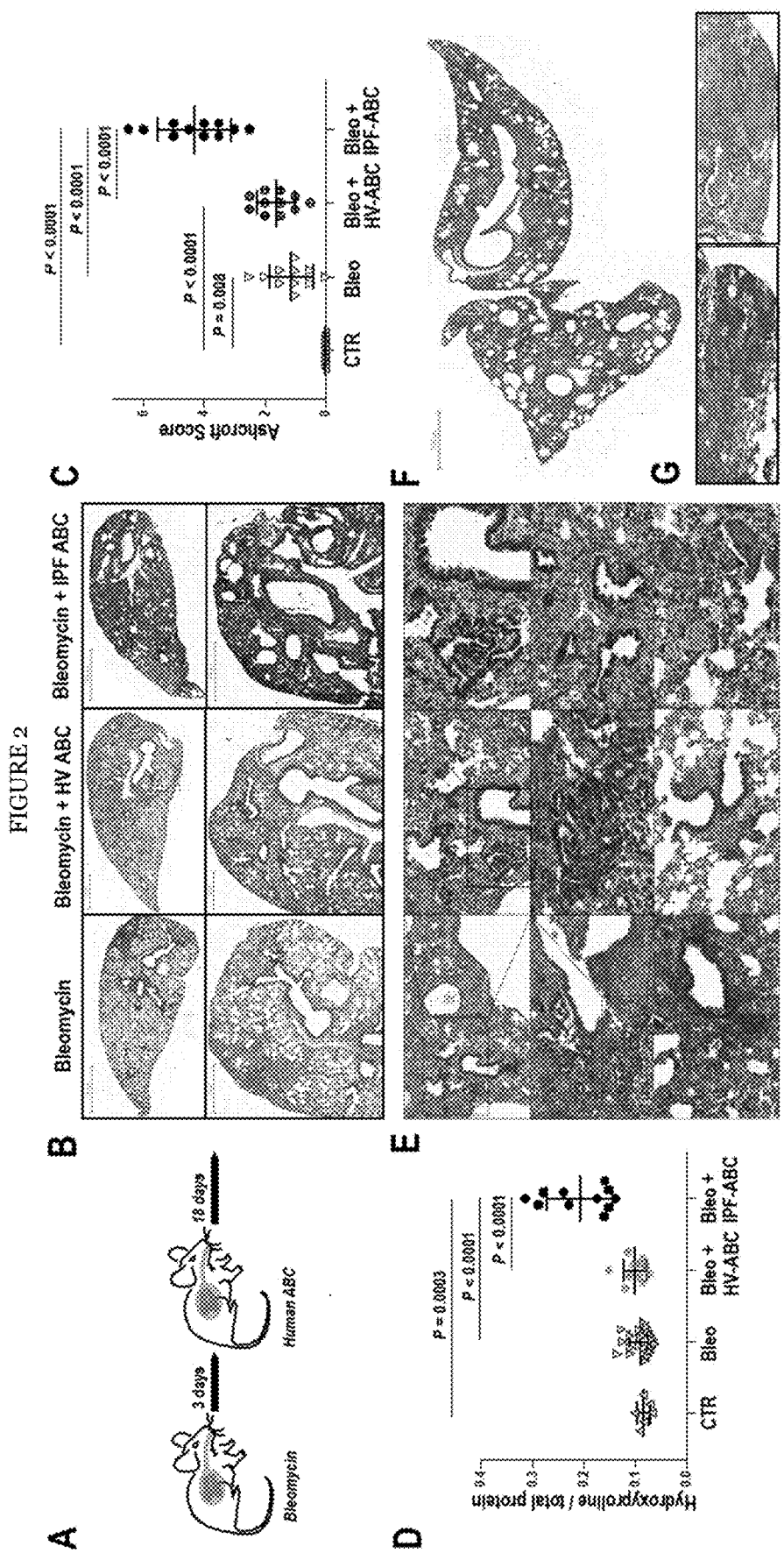
FIG. 2: Establishment of a humanized mouse model for IPF based on human ABCs. (A) Bleomycin (Bleo) was intratracheally administered to Rag2−/− mice (BL6 background). Three days later human airway basal cells (ABC) derived from either patients with IPF or HV were intratracheally administered. Lungs were harvested at day 21 following Bleo application. (B) Representative trichrome stainings of mice challenged with Bleo alone, Bleo and HV-ABCs or Bleo and IPF-ABCs. Fibrosis and cystic lesions are increased in mice challenged with Bleo+IPF-ABCs. (C-D) Ashcroft score and hydroxyproline levels were significantly increased in mice challenged with Bleo+IPF-ABCs (n=11) compared to mice challenged with Bleo and HV-ABCs (n=11) or Bleo alone (n=21). (E, F) Trichrome staining of mice injected with Bleo+IPF-ABCs, shown are representative lesions of 11 different mice. Bronchiolization of the alveolar compartment and de novo generation of airway structures is highly increased in these mice compared to mice challenged with Bleo alone or Bleo+HV-ABCs. These bronchiolar lesions look often bizarre and undirected. Others appear to resemble honeycomb cysts. New collagen synthesis (shown in blue) is seen predominately around the bronchiolar lesions. Rarely structures resembling fibroblast foci could be detected. (G) In some experiments with IPF-ABCs in NRG mice metaplastic squamous lesions evolved. (H) Mice were challenged with human IPF-ABCs transfected with a luciferase and GFP encoding vector (n=10, 3 replicates). Shown are representative bioluminescence measurements of luciferase expression in control NRG mice (Bleo) and NRG mice injected with transduced human IPF-ABCs and NU-ABCs (day 3-21). (I) Engraftment of human IPF-ABCs into venus expressing NSG lungs was detected by confocal microscopy. Human cytokeratin (hCK) 5/6, eGFP, CK8, nuclear DAPI and Venus-expression were detected. Human IPF-ABCs generate focal metaplastic lesions and pseudoglandular lesions in murine lungs. Some of the pseudoglandular lesions are also derived from murine cytokeratin (CK)8$^+$ airway epithelial cells. For statistical comparison (C, D) ANOVA with Tukey correction for multiple testing was used.
Figure 2:
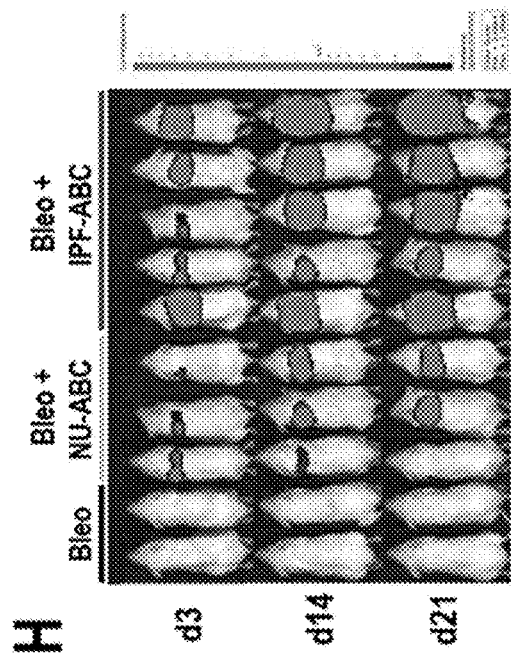
Figure 2:
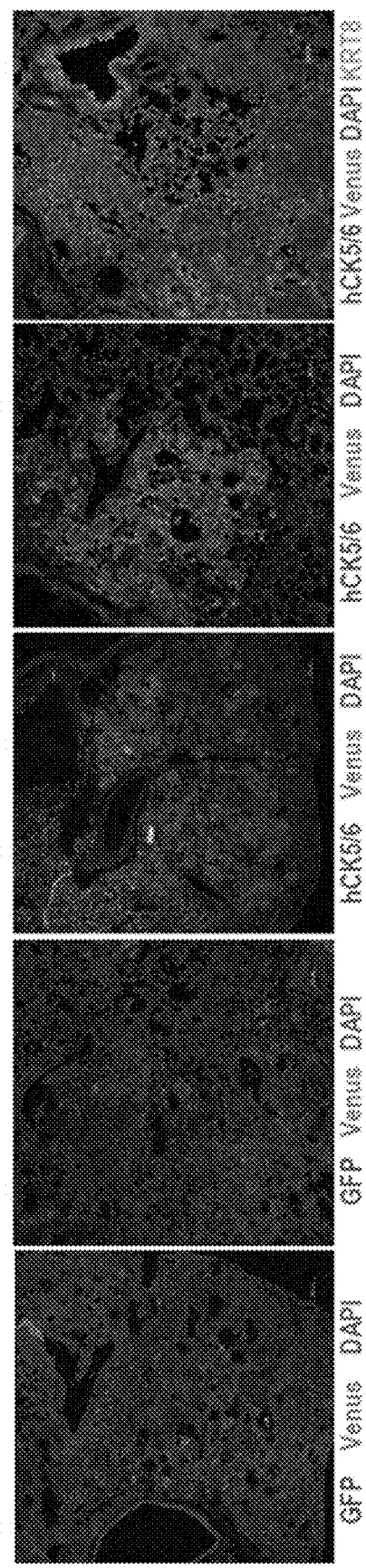

Example 3: Human IPF-ABCs Augment Bleomycin Induced Pulmonary Fibrosis and Induce Ultrastructural Changes in RAG2−/− and NRG Mice Intratracheal application of human IPF-ABCs or HV-ABCs to uninjured Rag2−/− mice and NRG mice had no discernible effect (data not shown). Thus, it was decided to administer the human IPF-ABCs or HV-ABCs three days after causing the lung minimal injury with a low dose of bleomycin to RAG2−/− mice (1.2 mg/Kg body weight IT, FIG. 2A). The administered bleomycin dose resulted in mild fibrotic changes in the lungs (FIG. 2B). IPF-ABCs administration highly increased bleomycin induced pulmonary fibrosis compared to HV-ABCs or bleomycin alone as shown by Masson trichrome staining (FIG. 2B). Ashcroft score (P<0.0001) and hydroxyproline levels (P<0.0001) were significantly increased in mice challenged with IPF-ABCs compared to mice challenged with HV-ABCs or bleomycin alone (FIGS. 2C and D). Similar results were obtained in NOD.Cg-Rag1tm1Mom Il2rgtm1Wjl/SzJZtm (NRG) mice. Masson trichrome staining showed abundant new collagen production centered around the airway structures but also reaching up to the pleura (FIGS. 2B and F). Starting with day 8 one could observed formation of de novo airway structures, areas of bronchiolization and formation of cystic structures (FIGS. 2E and F). Some of the induced lesions resemble pseudoglandular lesions described during lung development (FIG. 2E). As expected, engraftment and proliferation of human ABCs was enhanced in NRG mice. In NRG mice challenged with IPF-ABCs but not HV-ABCs we regularly observed focal squamous metaplastic lesions of human ABCs (FIG. 2G). In some experiments, NRG mice were challenged with human IPF-ABCs transfected with a luciferase and GFP encoding vector. Bioluminescence measurements of luciferase expression in mice injected with human IPF-ABCs (day 3-21) showed an increased signal intensity up to day 21 suggesting pulmonary engraftment of human cells and further proliferation (FIG. 2H). Introduction of GFP transduced IPF-ABC to the lungs of NOD.Cg-Prkdcscid Il2rgtm1Wjl Tg(CAGGS-VENUS)1/Ztm (NSG) venus expressing mice confirmed the engraftment of these cells in the murine lung building up focal squamous metaplastic and pseudoglandular lesions (FIG. 2I). Using NSG mice we were able to observe engrafted IPF-ABCs adjacent to murine origin areas of pseudoglandular structures, supporting an effect of IPF-ABC cells on host resident cells Example 4: Single Cell Sequencing of IPF-ABCs and NU-ABCs Identifies SRC as a Potential Therapeutic Target Single cell RNA sequencing (scRNASeq) was performed on cells obtained by bronchial brushing from nine IPF patients and six nonUIP disease controls. 14,873 epithelial single cell transcriptomes were profiled. Based on expression profiles of known marker the inventors identified four epithelial cell populations in the brushed cells (FIG. 3A-C): ciliated cells (FOXJ1, HYDIN, 41.5% of all epithelial cells), secretory cells (SCGB1A1, SCGB3A1, 10.5%), ABCs (TP63, KRT5, 47.1% of cells) and ionocytes (STAP1, PDE1C, 0.8% of cells) and focused the analysis on the basal cell.

Figure 3:
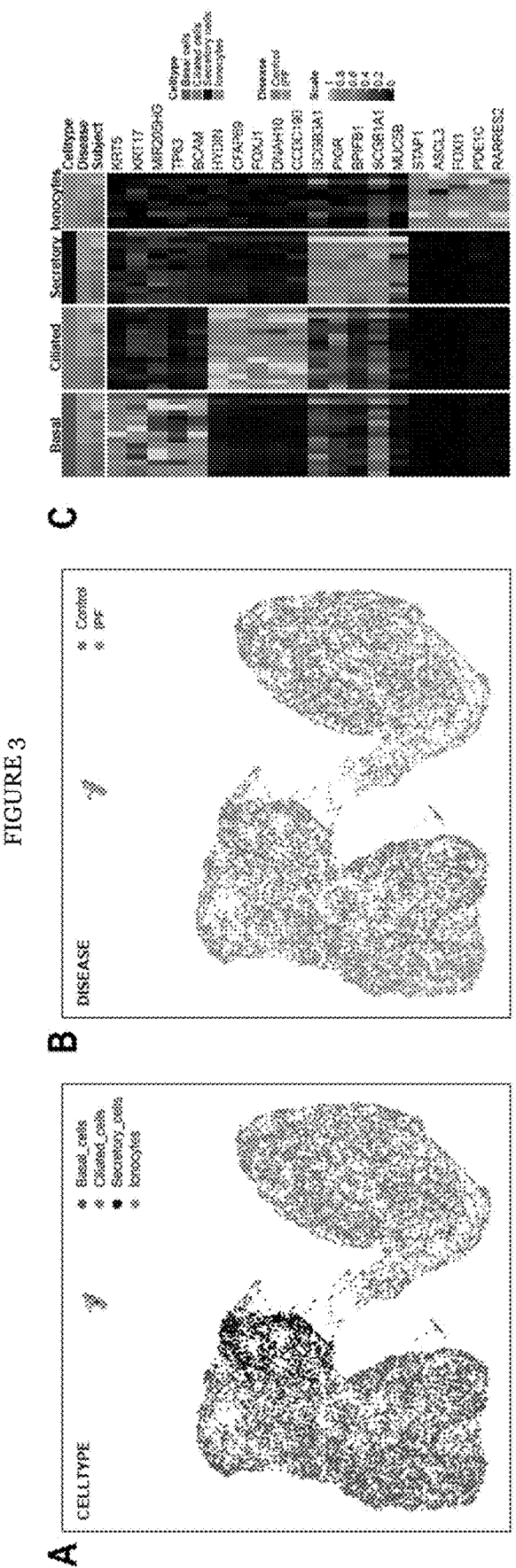
FIG. 3: Single cell RNAseq and Clue analyses of bronchial epithelial cells. Single cell RNA sequencing was performed on Brush cells of IPF patients (n=9) and nonUIP ILD controls (n=6). Uniform Manifold Approximation and Projection (UMAP) of 14,873 single cell transcriptomes visualizes the four major discrete epithelial cell types (detected UMAPs colored by (A) cell types, (B) disease state). (C) Heatmap of unity normalized canonical epithelial marker gene expression, averaged per subject, grouped by cell type, as shown in (A). (D) Heatmap of differentially expressed genes in ABCs of IPF patients vs nonUIP ILD disease controls showing a distinct deviation of gene expression (each column is a ABC, each row a gene as z-scores), (E) Violin plots of a subset of differentially expressed genes (DEGs) split by disease state. (F) Bar plots of summary CMap Connectivity scores of the clue.io analysis, dodged by input (ABC mortality signature—yellow, scSeq-derived DEGs IPF vs nonUIP ILD control in ABCs—blue). Inhibition of SRC had the lowest CMap Connectivity score, i.e. potentially reversing the input gene signatures.
Figure 3:
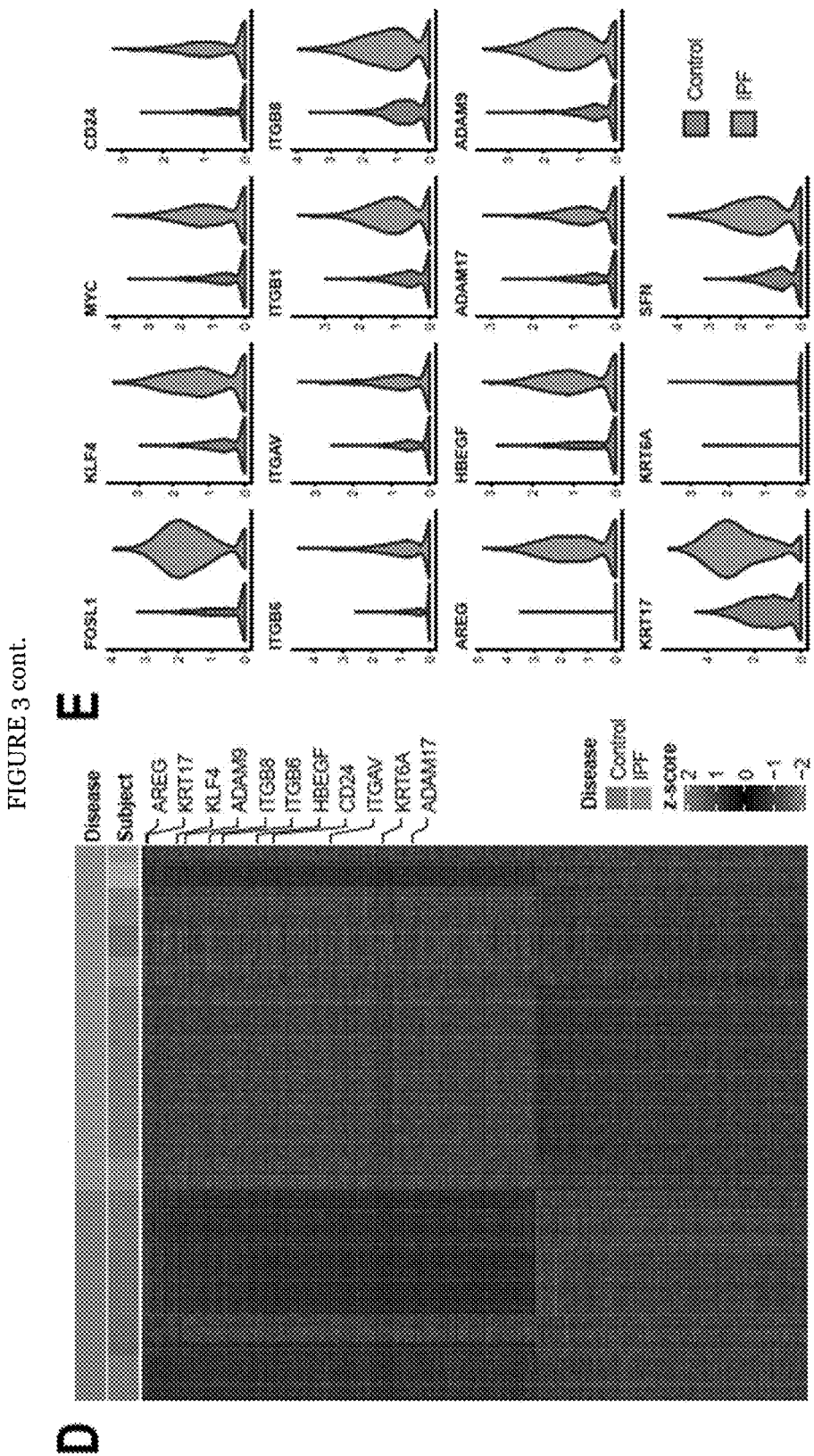
Figure 3:
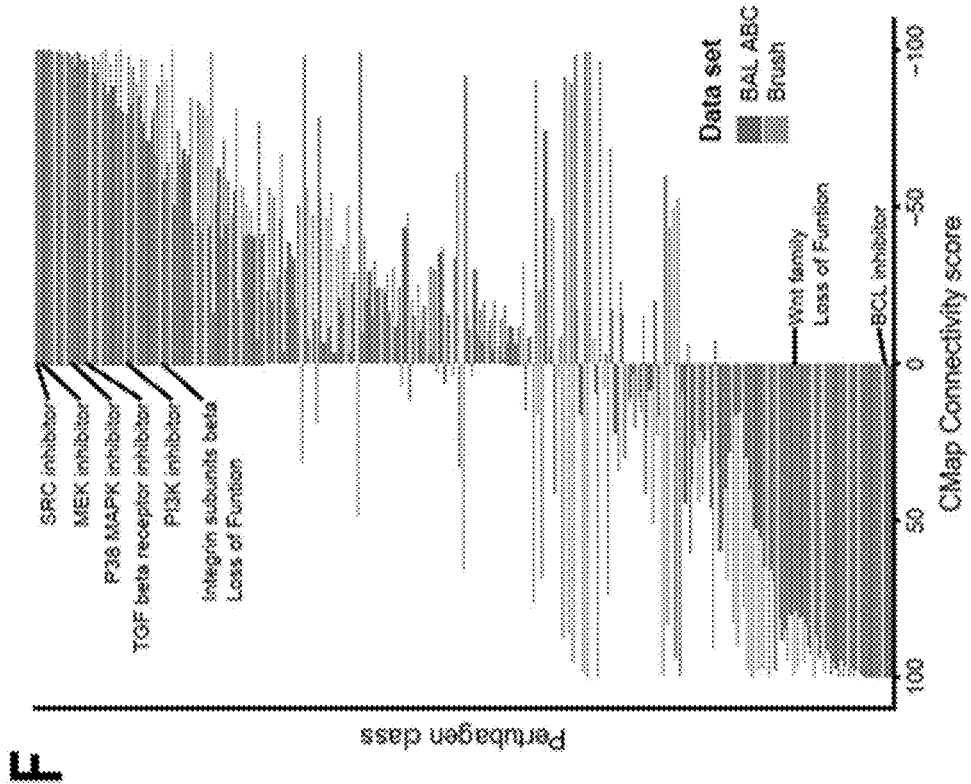

Gene expression of IPF-ABC was substantially different from NU-ABC (1,099 genes at FDR<0.05, FIG. 3D). The IPF basal cell subpopulation was characterized by an increased expression of stem cell markers and stemness increasing signal transduction factors such as FOSL1, KLF4, MYC, CD24 (FIGS. 3D and E), expression of KRT17 and stratifin (SFN) indicating a shift towards a squamous phenotype (FIGS. 3D and E) and expression of genes for integrin subunits such as ITGB6, ITGAV, ITGB1 and ITGB8 (FIGS. 3D and E). As expected based, increased expression of the EGF family members AREG and HBEGF and the shedding enzymes for amphiregulin, ADAM17, and for EGFR, ADAM9, was observed (FIGS. 3D and E). Connectivity MAP analysis using the gene expression profile of IPF-ABC identified a list of substance classes predicted to reverse this IPF-ABC signature: three perturbagen classes had a maximum summary connectivity score of −100: SRC-inhibitors, MEK-inhibitors and loss of function of C2 domain containing protein kinases (FIG. 3F).

Figure 4:
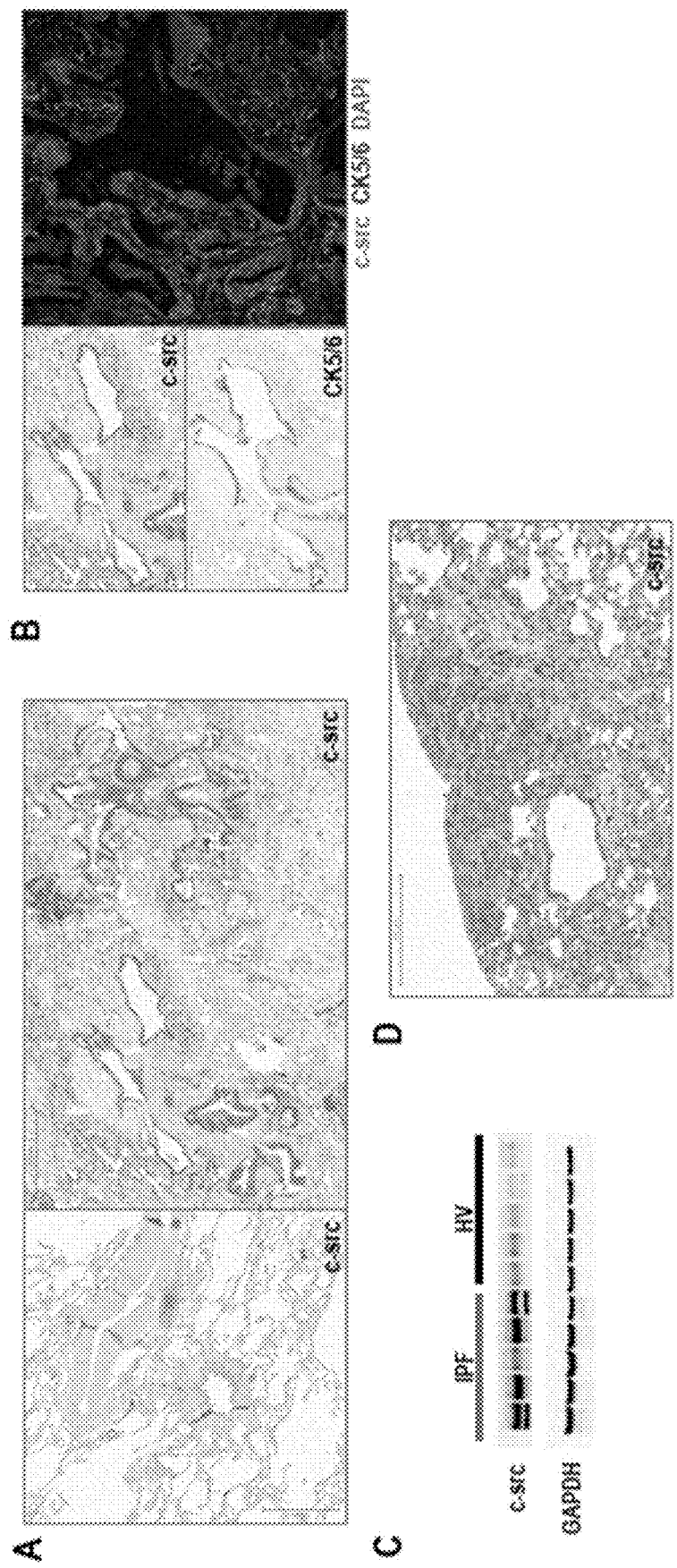
FIG. 4: Overexpression of c-src in IPF lungs and cellular effects of c-src over-expression and knockout. (A) In normal human lung tissue c-src expression was low, only few macrophages were stained positively. In contrast c-src expression of IPF lung tissue was high. Macrophages and epithelial cells highly expressed c-src as well as lymphocytes within lymphoid follicles. (B) Most of the epithelial cells expressing c-src were also positive for CK5/6 identifying them as basal cells. (C) c-src expression was high in lung tissue homogenates of IPF patients compared to healthy donors. (D) Immunohistochemistry of murine lungs of the described humanized mouse model also showed high c-src expression of macrophages and airway epithelial cells. (E) C-src expression was either overexpressed, untouched (EV) or knockout in human ABCs using a lentiviral vector and resulting c-src expression was measured using Western blot. (F, G) C-src overexpression in human IPF-ABCs which were injected into NRG mice lead to increased pulmonary fibrosis, while knockout of c-src downregulated the induced fibrosis (mean±SD, n=6, each group, 2 replicates). For statistical comparison repeated measures ANOVA with Tukey correction for multiple testing was used.
Figure 4:
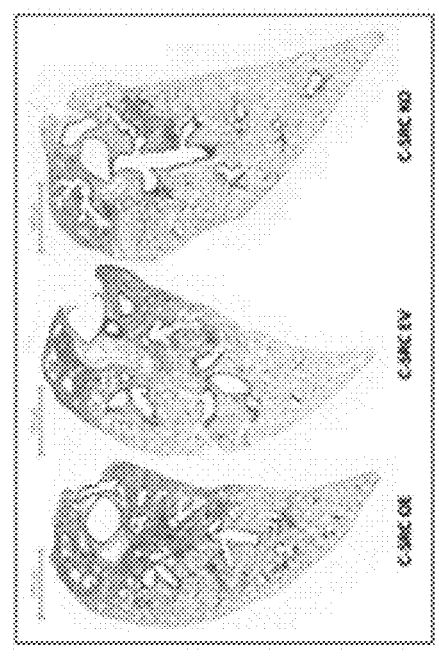
Figure 4:
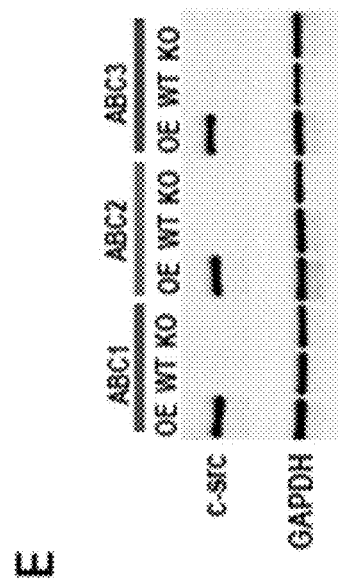
Figure 4:
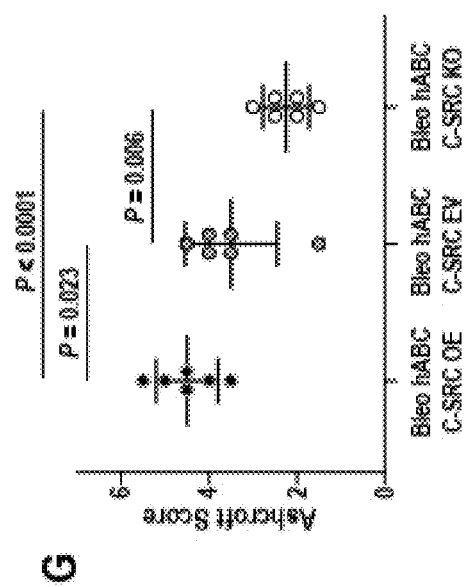

Example 5: SRC Expression is Increased in Lung Tissues of IPF Patients and Murine Lungs of the Described Humanized Mouse Model Based on the results of the described in-silico analyses, the inventors analyzed SRC protein expression in IPF-tissues and ABCs. SRC was highly increased in IPF lung tissues (FIGS. 4A and B), specifically in epithelial cells covering fibroblast foci and within areas of bronchiolization. SRC staining of macrophages was observed in both IPF and control lungs (FIGS. 4A and B). SRC was increased in lung homogenates of IPF lung tissues compared to healthy lung tissue (FIG. 4C). Impressively, SRC protein expression was also observed in the xenograft IPF-ABC mouse model described above, primarily in areas of aberrant airway generation, bronchiolization and in pseudoglandular lesions (FIG. 4D). As expected, SRC staining of macrophages was also observed in the mouse lung (FIG. 4D).

Example 6: SRC Overexpression in IPF Airway Basal Cells Increased Cell Invasion and Fibrosis, while SRC Knock-Down Attenuated Fibrosis IPF-ABCs were transduced with different vectors which lead to overexpression of SRC, knockdown of SRC or expression of GFP as control (empty vector (EV)). Effects on SRC expression were confirmed by Western blot (FIG. 4E). We then tested the effects of modifying SRC expression in IPF-ABCs on fibrosis in the IPF-ABC xenograft model described above. Forced overexpression of SRC in IPF-ABCs (SRC$^+$ IPF-ABC) resulted in enhanced fibrosis and cellular remodeling in the alveolar compartment of NRG mouse lungs, whereas SRC knockdown in IPF-ABC cells (SRC$^-$ IPF-ABC) from the same donor caused markedly reduced remodeling (FIG. 4F). Quantification of these results using the Ashcroft score confirmed both, a significant increase in fibrosis in SRC$^+$ IPF-ABC and a decrease in fibrosis in SRC$^-$ IPF-ABC compared to controls (P=0.023, P=0.006, respectively FIG. 4G).

Figure 5:
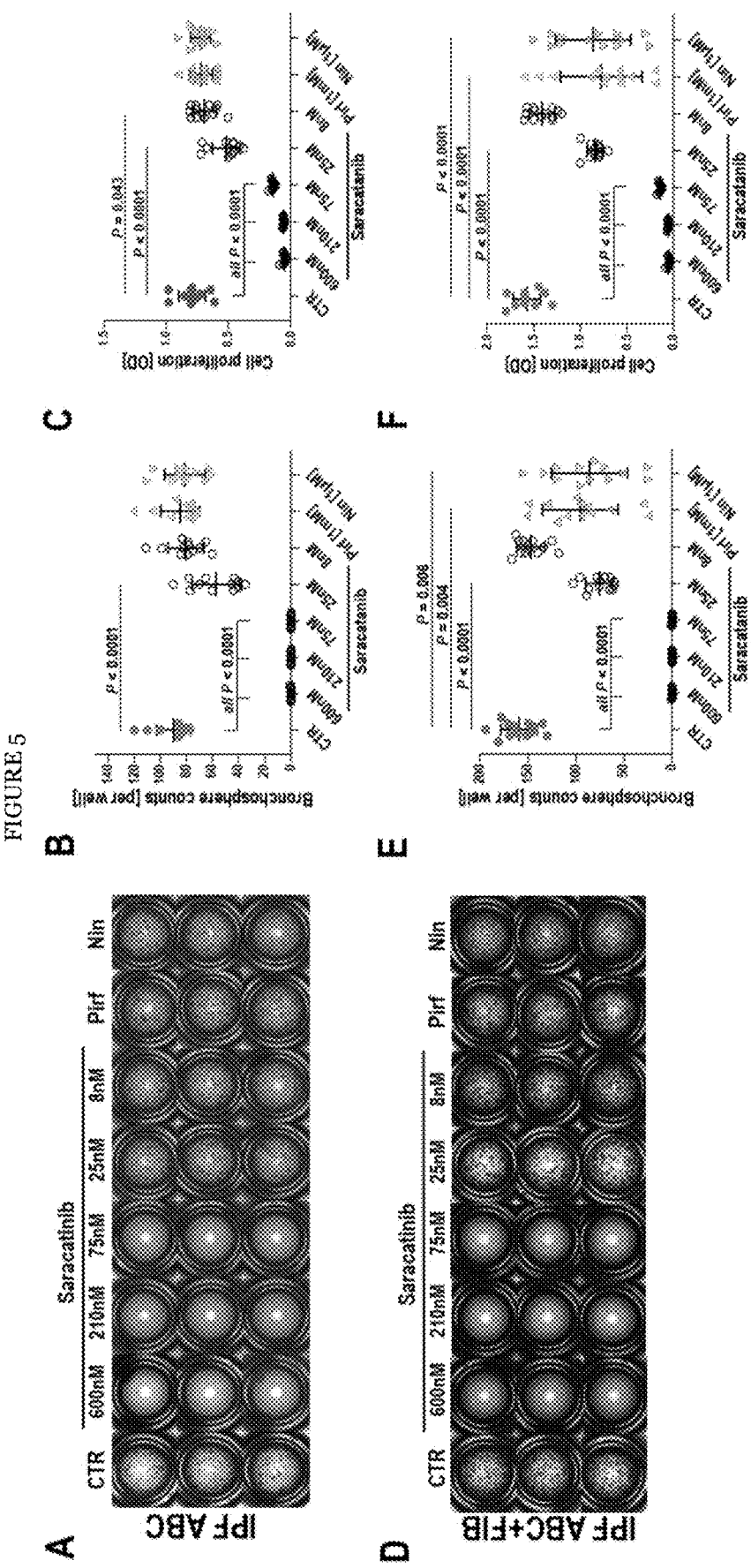
FIG. 5: SRC-inhibitor saracatinib abrogates bronchosphere formation. (A-E) Bronchosphere assays of human IPF-ABCs were performed w/wo IPF lung fibroblasts for 21 days. Cell cultures (n=12, in triplicates) were treated with either vehicle, saracatinib (600, 210, 75, 25, 8 nM), pirfenidone (1 mM) or nintedanib (1 μM). (B) Saracatinib abrogated sphere formation dose-dependently while a dose of pirfenidone or nintedanib, which was higher than usually applied in humans, did not change bronchosphere counts (mean±SD). (C) Cell proliferation as measured by MTI assay was significantly reduced by saracatinib treatment in a dose dependent manner and slightly by pirfenidone and nintedanib (mean±SD). (D, E) Saracatinib treatment also abrogated sphere formation dose-dependently in the presence of IPF lung fibroblasts while pirfenidone and nintedanib reduced significantly, but not abrogated, sphere formation in the presence of fibroblasts (mean±SD). (F) Cell proliferation as measured by the MTT assay was significantly reduced by saracatinib treatment in a dose dependent manner and less reduced by nintedanib or pirfenidone treatment (mean±SD). (G, H) In the same model we used GFP$^+$ fibroblasts to study fibroblast proliferation. Saracatinib treatment also showed a dose-dependent effect upon fibroblast proliferation (mean t SD, n=4, 2 replicates). For statistical comparison repeated measures ANOVA with Tukey correction for multiple testing was used.
Figure 5:
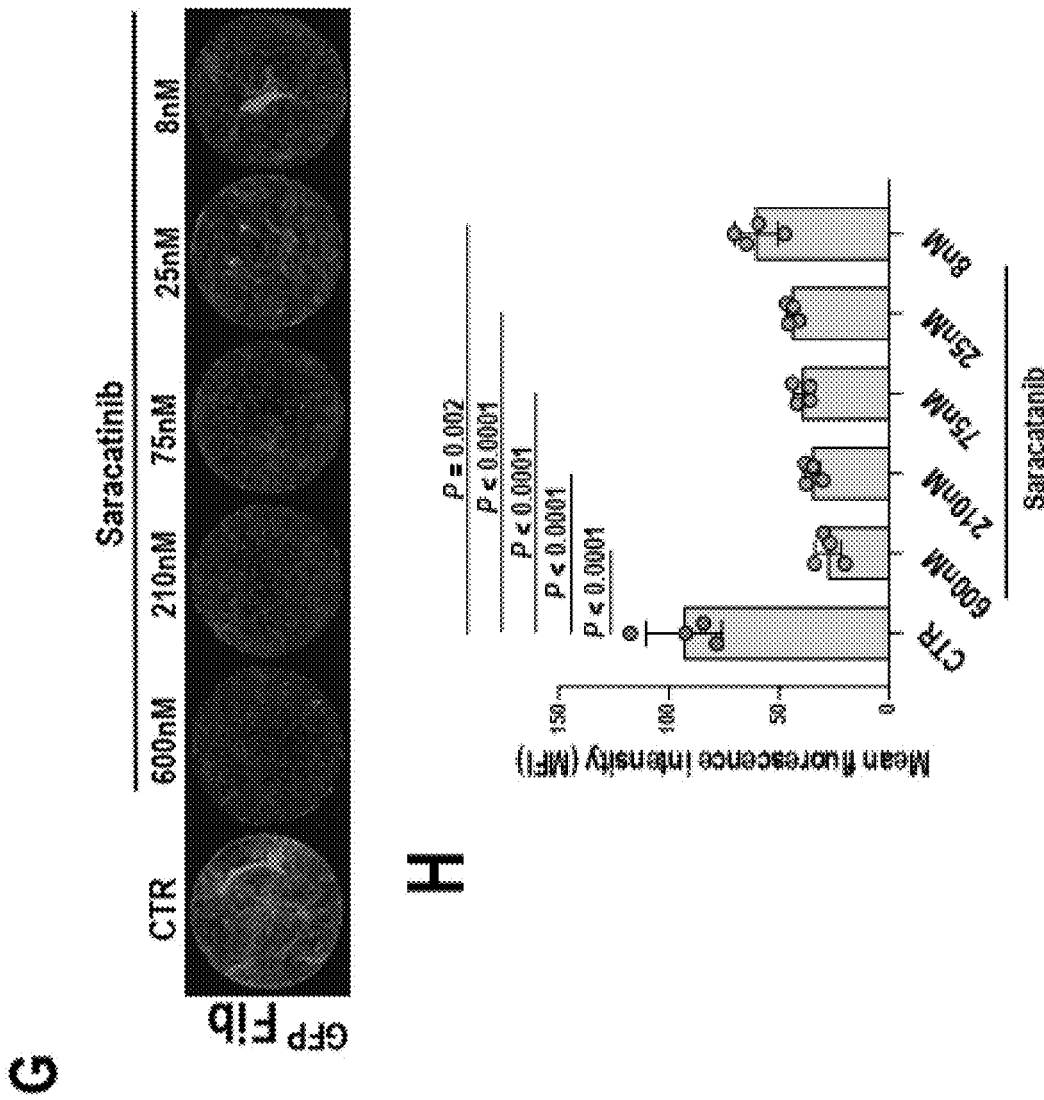

Example 7: The SRC Inhibitor Saracatinib Completely Abrogates IPF-ABC Bronchosphere Formation and Attenuates Fibroblast Proliferation In-Vitro Based on the Connectivity MAP predictions, the inventors tested whether saracatinib, a known SRC inhibitor previously tested in human cancer is able to modulate IPF-ABC phenotype. When IPF-ABC were cultured in 3D and were treated with saracatinib, nintedanib, pirfenidone or vehicle, a complete abrogation of bronchosphere formation at saracatinib concentrations of 600 nM, 210 nM, and 75 nM was observed, whereas nintedanib and pirfenidone had no visible effect on bronchosphere formation (FIG. 5A). The results were similar in cells obtained from 12 different individuals with IPF (P<0.0001, FIG. 5B). Saracatinib did not affect cellular vitality of ABCs in all used concentrations (FIG. S5) and these concentrations were considered equivalent to clinically relevant doses. Similar data were obtained by testing cell proliferation in the MTT assay (P<0.0001, FIG. 5C). In the co-culture model of IPF-ABC with lung fibroblasts, saracatinib completely blocked bronchosphere formation at the concentrations of 600 nM, 210 nM and 75 nM, had a lower effect at 25 nM, and did not have an effect at 8 nM (FIG. 5D-F). In contrast to the single culture model described above, in the IPF-ABC fibroblast co-culture model, pirfenidone and nintedanib significantly reduced bronchosphere formation, but not completely (FIG. 5D-F), potentially reflecting an effect of these drugs on the fibroblast component of this interaction. Fibroblast proliferation in the co-culture was also substantially lower in the presence of saracatinib (FIGS. 5G and H).

Example 8: Saracatinib Attenuated Fibrosis and Bronchialization In-Vivo

Figure 6:
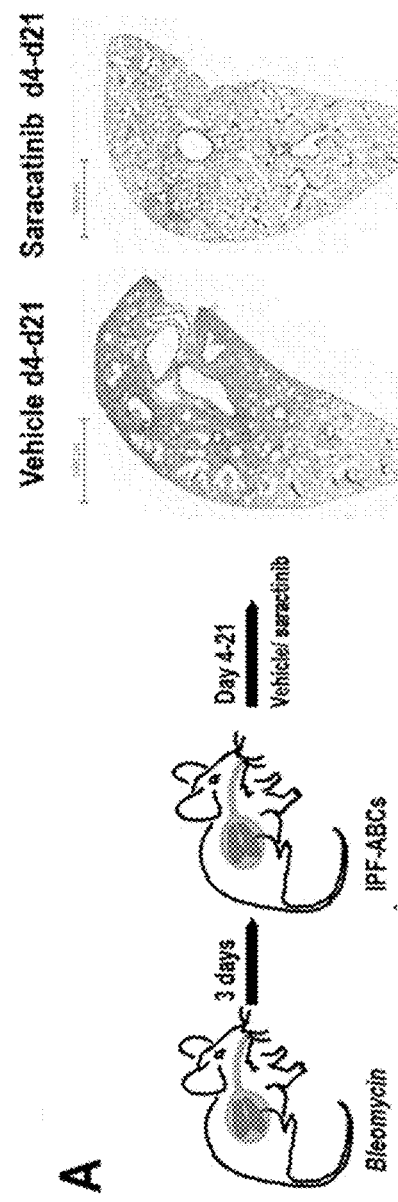
FIG. 6: SRC-inhibitor saracatinib attenuates fibrosis in the humanized mouse model. NRG mice were intratracheally injected with a low dose of bleomycin and 3 days later with human ABCs derived from IPF patients. Mice (n=11 each group, 4 replicates (all data shown)) were treated oropharyngeally with or without saracatinib in a dose of 10 mg/kg once daily starting at day 4 (A-C) or at day 8 (D-F). (A-C) Treatment with saracatinib from day 4 significantly reduced the evolution of fibrosis as measured by Ashcroft score (B, mean t SD) and hydroxyproline levels (C, mean±SD). (D-F) Saracatinib treatment from day 8 to day 21 also significantly reduced fibrosis but effect was less than with immediate treatment as measured by Ashcroft score (E) and hydroxyproline levels (F). All P values were determined by a paired comparison (t-test) testing the effect of saracatinib treatment for each human IPF cell line.
Figure 6:
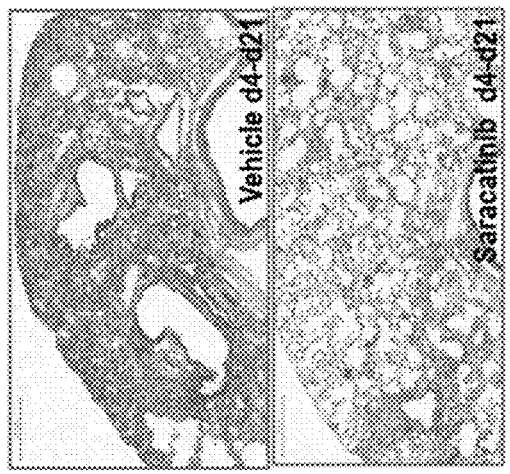
Figure 6:
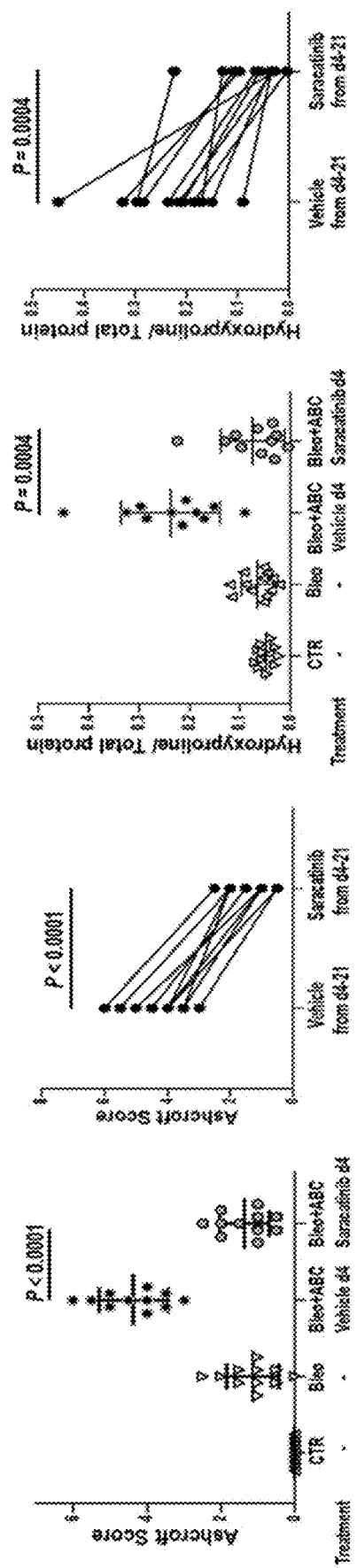
Figure 6:
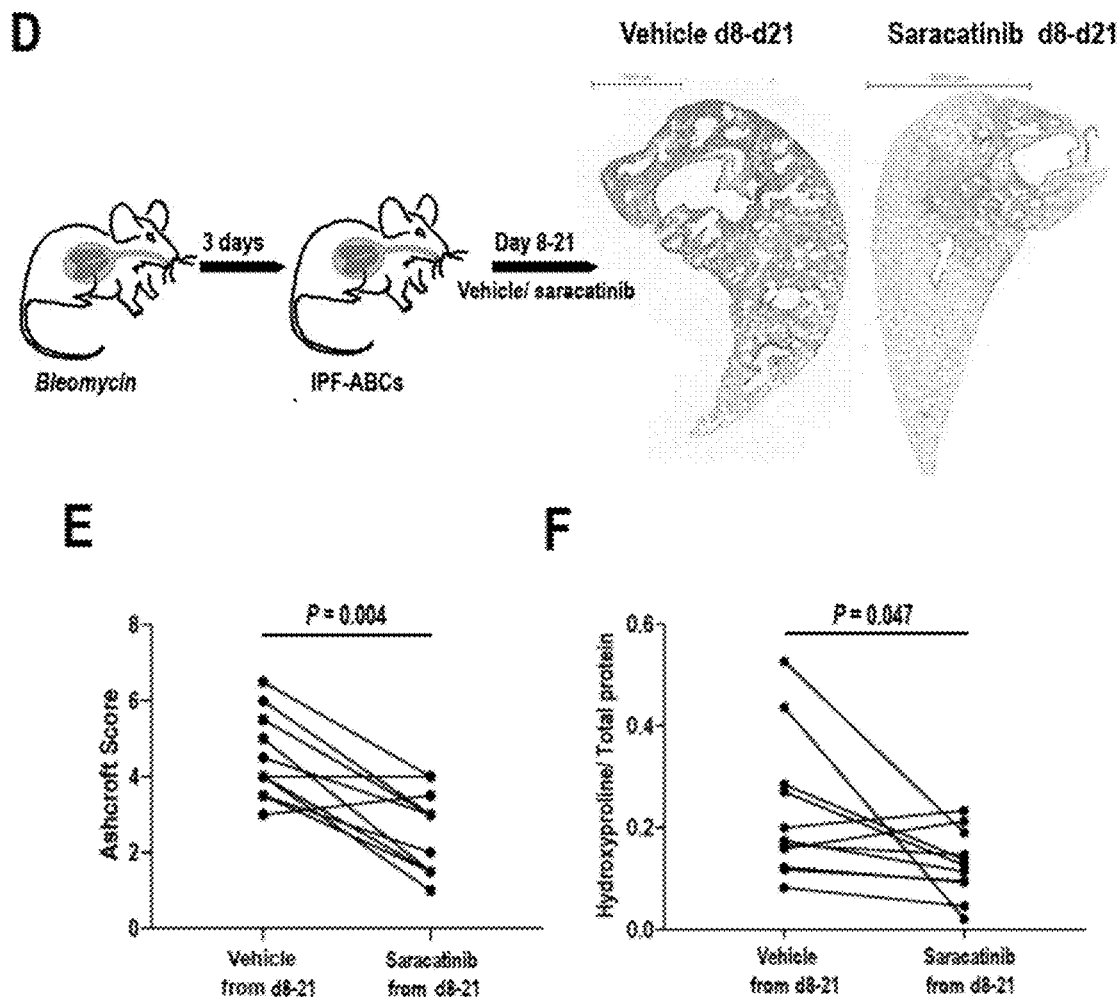

To test the effect of saracatinib on IPF-ABC induced fibrosis and remodeling in-vivo, the inventors returned to the minimal injury xenotransplant model in NRG mice. Overall, the inventors used IPF-ABCs from 38 different individuals with IPF in these experiments. Per IPF subject, IPF-ABCs were used in two animals, one treated with saracatinib and one with vehicle control, to account for interindividual variability. To test the effect of saracatinib on engraftment and development of fibrosis we started treatment at day 4 post injury, one day post IPF-ABC installation for a total of 18 days (FIG. 6A). Oropharyngeal saracatinib in a dose of 10 mg/kg once daily significantly reduced fibrosis at day 21 as measured by Ashcroft score (4.4±0.9, 1.4±0.7, P<0.0001, FIG. 6B) and hydroxyproline/total-protein levels (2.4±1.0, 0.7±0.6, P=0.0004, FIG. 6C). To test the effect of saracatinib on established fibrosis the inventors performed another set of experiments in which treatment was delayed to day 8 when cell engraftment and fibrosis were already established. Saracatinib treatment again significantly reduced remodeling and fibrosis (FIG. 6D) as was reflected by significant reductions in the Ashcroft score (P=0.04, FIG. 6E) and hydroxyproline content (P=0.047, FIG. 6F).

DISCUSSION

In this application the inventors show that airway basal cells which are found in areas of remodeling and bronchiolization and adjacent to fibroblastic foci in the IPF lung have unique profibrotic properties. Using a 3D organoid model, it is demonstrated that IPF-ABCs give rise to more bronchospheres compared to normal or nonUIP ILD cells. Co-culture experiments with fibroblasts show a close interaction of both cell types which results in augmented bronchosphere formation by IPF-ABC as well as enhanced proliferation and extracellular matrix (ECM) deposition by fibroblasts. Intratracheal application of IPF-ABCs into minimally injured lungs of immunocompromised mice leads to severe fibrosis and remodeling of the alveolar compartment including the evolution of honeycomb cyst-like structures. Transcriptionally, IPF-ABCs are substantially different and exhibit enhanced stemness, ECM sensing and EGF signaling. Connectivity analysis suggested that gene expression changes in IPF-ABCs can be reversed by SRC inhibition and enhanced SRC expression and activity were observed in IPF lungs. Saracatinib, a potent SRC inhibitor, modulated the in-vitro and in-vivo IPF-ABC induced profibrotic changes.

In this in this application there is provided the first demonstration that ABCs from patients with IPF are functionally different and have profibrotic effects in-vivo and in-vitro. ABCs are considered an airway stem cell population, capable of proliferation and self-renewal and can give rise to all types of airway epithelial cells. Moreover, ABCs have been implicated in COPD, asthma and lung cancer. The invention shows several lines of evidence that IPF-ABCs have substantial profibrotic properties. The first clue comes from the observation that unlike HV-ABCs or NU-ABCs, IPF-ABCs generate numerous, well developed and multi-layered bronchospheres in the 3D culture model system. This in-vitro model is widely used in oncology and developmental biology as an indicator of cellular stemness in formation of tumor spheres and organoids. The data demonstrates that ABCs of IPF patients differ from those of healthy volunteers by their enhanced capacity to from bronchial like structures in vitro that potentially reflect an exaggerated stem cell phenotype of these cells. This is also supported by the scRNAseq results, as IPF-ABCs overexpress known stemness genes; such as KLF4, a transcription factor used for induction of pluripotency and known to be associated with stemness and epithelial-mesenchymal transition (EMT) (26, 27); MYC, a transcription factor also used for induction of pluripotency and stemness (27, 28); TCF4 which closely interacts with β-catenin and is important for stem cell renewal (29-31); AP1 forming c-JUN and FOSL1 (also known as the proto-oncogene c-fos) which are downstream transcription factors of genes inducing pluripotency (27, 32, 33) and important oncogenes for cancer stem cells (34). The second line comes from the co-culture experiments that suggested a self-amplifying interaction between ABCs and fibroblasts. The presence of lung fibroblasts, increased evolution of bronchospheres, whereas ABCs stimulated proliferation and collagen production of fibroblasts. In both cases, the effect was stronger when the cells used were obtained from individuals with IPF. The data suggests that one mechanism contributing to this phenomenon involves the EGFR axis—scRNAseq revealed that amphiregulin expression is significantly increased in IPF-ABCs compared to NU-ABCs and that the bronchospheres generated from IPF-ABCs secrete significantly higher concentrations of amphiregulin compared to both HV-ABCs and NU-ABCs. Conditioned media from IPF-ABC bronchosphere cultures induced phosphorylation of EGFR in fibroblasts. Generally, the role of EGFR ligand family members in fibrosis has been studied mainly in other organs with sometimes conflicting results. However, amphiregulin has been most consistently shown profibrotic effects in models of liver, kidney and heart fibrosis. In the lung, amphiregulin was proposed as a mediator of TGFB1 mediated pulmonary fibrosis in the triple transgenic mouse model, but without significant follow up. The present results suggest that amphiregulin may be a frequently overlooked major mediator of the interaction of ABCs and fibroblasts in fibrosis. The third line of evidence comes from the humanized model of lung fibrosis that is established in the present disclosure. Human IPF-ABCs, but not HV-ABCs, induced abundant bronchiolization, airway enlargement, cyst formation and frequently pleural extending fibrosis, hallmark features of UIP histology missing in commonly used animal models of pulmonary fibrosis. The model clearly demonstrates that IPF-ABCs induce a vast remodeling and deconstruction of the murine alveolar lung architecture. Taken together these lines of evidence support the unique profibrotic properties of ABCs obtained from lungs of patient with IPF.

There is reason to assume that cigarette smoking, exposure to other environmental factors, recurrent airway infections and genetic background may lead to airway epithelial barrier injury in IPF which then may have an impact on ABC gene expression as recently described for asthma and TH2 inflammation. Genetic risk factor for IPF such as polymorphisms in MUC5B, desmoplakin and AKAP13 are linked to epithelial barrier function and AKAP13 and desmoplakin, unlike MUC5B, are highly expressed by ABCs. The scRNAseq data demonstrate increased expression of the stress induced keratins CK6 and CK17, upregulation of key molecules of epithelial barrier function (claudin 1 and 4), of several integrins which regulate ECM composition (β6, vα, β1, α4, α6 and α2), markers of epithelial cells senescence such as GDF15, and the EGFR ligands AREG and HBEGF in IPF-ABCs. Thus, the transcriptional phenotype of IPF-ABCs may represent the end results of the lung response to repetitive epithelial injuries, which trigger exaggerated repair processes including increased stemness and epithelial-mesenchymal crosstalk.

Another novel feature of this study is the focus on SRC inhibition in pulmonary fibrosis and especially as mediator of IPF-ABC profibrotic effects. Based on our scRNAseq data and our recently published BAL data set we tested for potentially beneficial drug candidates using connectivity map. The in-silico analyses indicated that SRC-inhibitors may be capable of reversing the profibrotic basal cell phenotype which we observe in IPF. SRC is a hub integrating multiple pathways including integrin and receptor kinase signaling, and results in phosphorylation of various substrates such as STAT3, FAK, JNK, EGR, AKT, and PI3K. SRC kinase activity is increased in multiple cancers and linked to proliferation, migration and invasion of cells. SRC was also shown to align to the EGFR molecule to facilitate it's signaling both upstream and downstream and is linked to stemness of cancer cells. SRC signaling is closely linked to epithelial injury induced by various noxious agents including cigarette smoking. A role for SRC has been proposed in in fibrosis in multiple organs but most of this work focused on the role of SRC in fibroblasts. The inventors found abundant SRC expression in ABCs covering the fibroblast foci in IPF lungs. Overexpression of SRC in ABCs resulted in an increase in fibrosis and knockout of SRC reduced fibrosis in our humanized mouse model of IPF. Herein the SRC inhibitor saracatinib was tested (AZD0530) in the in-vitro and in-vivo models. Saracatinib completely abrogated sphere formation in the 3D organoid model. In the co-culture model, saracatinib had an effect on both sphere formation and fibroblast proliferation suggesting that SRC inhibition by saracatinib may disrupt the profibrotic HV-ABCs crosstalk between IPF-ABCs and fibroblasts. Similar effects were also observed in our humanized mouse model, where saracatinib substantially attenuated IPF-ABC induced pulmonary fibrosis, bronchiolization and cyst formation. This effect was also observed when saracatinib was administered during established fibrosis. Taken together, these findings suggest that saracatinib treatment efficiently blocked human IPF-ABC engraftment and proliferation.

In conclusion, the data indicates a profibrotic role of ABCs in IPF. In recent years there has been a significant increase in the understanding of the mechanisms of pulmonary fibrosis. Roles for distinct lung cell populations such as fibroblasts and myofibroblasts, macrophages and even alveolar epithelial cells have been proposed. While, ABCs have been noticed in the IPF lung, mechanistic studies evaluating their properties, and role in pulmonary fibrosis have been missing. The present results provide clear evidence that human IPF-ABCs have profibrotic properties in-vitro and in-vivo, and that interventions that address their properties inhibit occurrence of fibrosis or reverse fibrosis. These findings position the ABC as a key cell in the pathogenesis of certain human pulmonary fibrosis and other lung disease and thus a novel cellular target for therapeutic interventions.

Materials and Methods
Study Population

For the described experiments in total bronchial brushes from 68 patients with IPF, 25 patients with nonUIP fibrotic ILD and 18 healthy volunteers of an older age (>50 years) were obtained. IPF diagnosis was established by a multidisciplinary board according to the ATS/ERS criteria (3, 72). The study was approved by local ethics committees and all included individuals signed informed consent. For more details see supplement.

Immunohistochemistry

Immunohistochemistry of lung tissues was performed using a standard protocol and as recently described (16). Detailed information is given in the supplement.

Isolation of Airway Basal Cells

Airway basal cells were isolated from bronchial brushes of sub-segmental bronchi of the right lower lobe as recently described (73). Detailed information regarding cell isolation is given in the supplement.

Human 3D Bronchosphere Assay

ABCs, either derived from IPF patients or HV, were cultured in matrigel (Corning) in a transwell system with or without lung fibroblasts either derived from patients with IPF or normal lung for 21 days (if not otherwise indicated) in the incubator (5% CO2, 37° C.). Medium exchange (BEGM (Lonza, Basel, Switzerland, #CC-3170)/DMEM (Dulbecco's Modified Eagle Medium (Gibco, Swit Fisher Scientific/Germany); ratio 1:1) was done every 7 days. In some experiments lentiviral transduced GFP expressing fibroblasts were used. Conditioned medium of the 3D organoid culture (day 7 and day 14) was used for ELISA and fibroblast stimulation experiments. Sircol assay (Scientific-Biocolor/UK, #S1000) was performed as recommended by the manufacturer on matrigel and conditioned medium harvested after 6 weeks of cell culture. Bronchosphere formation was documented by Axio Vert.A1/Zeiss/Germany and Axio Observer Z1/Zeiss/Germany. For histology, immunohistology and confocal laser microscopy 3D cell cultures were cryopreserved using Tissue-Tek and cryomolds (Hartenstein/Germany; #CMM). Detailed information is given in the supplement.

Single Cell RNA Sequencing of Brush Cells

Single cell sequencing libraries of brush cells from nine IPF patients and six non UIP ILD control patients were generated as previously described (74) using the lox Genomics Chromium Single Cell 3' v2 kits according the manufacturer's instructions. Libraries were pooled and sequenced on an Illumina HiSeq 4000 aiming for 150 million reads per library. zUMIs pipeline was used for subsequent processing of reads. Data analysis and visualization were performed using the R package Seurat. Gene expression of ABCs of IPF and nonUIP ILD controls were compared using a Wilcoxon Rank Sum test with Bonferroni correction of p-values for multiple testing.

Connectivity Map (CMap) Analysis

Broad Institute's CLUE platform (https://clue.io) was used to identify a potential molecular mechanism of action which could reverse A) the deviating gene expression profile of ABCs in IPF as identified by scSeq in this study and B) the ABC gene expression signature associated with mortality in IPF by bulk RNA sequencing as recently described by us (16). Pertubagen classes were extracted and visualized as bar plots of the summary connectivity scores split by the origin of the input gene profiles.

Humanized Pulmonary Fibrosis Model with Intratracheal Administration of Human ABCs into Mice In-Vivo Different mice strains were used for the experiments as indicated. B6;129Sv-Rag2tm1Fwa/ZTM (75) (Rag2−/−) and NOD.Cg-Rag1tm1Mom Il2rgtm1Wjl/SzJZtm (76) (NRG) were obtained from the central animal facility (Hannover Medical School, Hannover). NOD.Cg-Prkdcscid Il2rgtm1Wjl Tg(CAGGS-VENUS)1/Ztm (Venus-NSG) mice were kindly provided by Dr. Wiebke Garrels (Hannover Medical School). Mice received bleomycin dissolved in sterile saline at the dose of 1.2 mg/kg intratracheally on day 0. IPF-ABCs, HV-ABCs (Rag 2−/−: 0.3×105, NRG and NSG: 0.2×105) were injected intratracheally on day 3. In some experiments human IPF-ABCs transduced with a lentiviral vector encoding for GFP and luciferase were injected. Pairs of mice received the same IPF-ABC line and were later treated either with vehicle or saractinib (kindly provided by Leslie Cousens AstraZeneca) in a dose of 10 mg/kg, i.g. once daily. For histological and immunohistological analysis, the trachea was cannulated and lungs were insufflated with 4% paraformaldehyde in PBS at a pressure of 25 cm H2O, followed by removal of the heart and inflated lungs en bloc and immersion in 4% paraformaldehyde overnight at 4° C., and the tissues were processed to paraffin wax or were cryopreserved using Tissue Tek® O.C.T.™ compound. H&E, Masson trichrome stains and Ashcroft score were performed according to a standard protocol (77, 78). Collagen content was determined by quantifying hydroxyproline levels according to manufacturer's description. For further details, see supplementary information

The invention claimed is:

1. A method for the treatment of a subject, the method comprising reducing a pathological capacity of airway basal cells (ABC) for bronchosphere formation by administering to the subject an effective amount of a compound, wherein the compound is an MEK inhibitor, an SRC inhibitor, a C2-domain containing protein, kinase, an LOF, a Rho-associated kinase inhibitor, a PARP inhibitor, a GPCR subset GOF, a JAK3 inhibitor, an HSP90 inhibitor, a topoisomerase II inhibitor, an HMGCR inhibitor, a mediator complex LOF, a PKA inhibitor, an IGF-1 inhibitor, a TGF-beta receptor inhibitor, a VEGFR inhibitor, a P38 MAPK inhibitor, an S100 calcium binding protein LOF, an integrin subunit beta LOF, a beta-adrenergic receptor agonist, a bromodomain inhibitor, an EGFR inhibitor, or an RAF inhibitor;

or the compound is selected from the group consisting of: Y-27632, PD-98059, tivozanib, PTB1, UNC-0321, tofacitinib, phenazopyridine, selumetinib, apigenin, erythrosine, Cyclo-[Arg-Gly-Asp-D-Phe-Val], fasudil, PP-2, SB-202190, TWS-119, 9-methyl-5H-6-thia-4,5-diaza-chrysene-6,6-dioxide, fostamatinib, EMF-bcal-60, CG-930, AZ-628, RG-13022, sildenafil, FR-180204, PD-0325901, GSK-429286A, MEK1-2-inhibitor, PP-1, tyrphostin-AG-112, FTI-276, tipifarnib, myriocin, AS=703026, TPCA-1, atorvastatin, baeomycesic-acid, LY-364947, xanthoxyline, fatostatin, PD-0325901, RHO-kinase-inhibitor-III[rockout], lovastatin, BMS-536924, PKCbeta-inhibitor, PD-184352, PJ-34, simvastatin, JAK3-inhibitor-I, PCA-4248, KIN001-242, WH-4023, SIB-1757, phenothiazine, AS=605240, saracatinib, U0126, JZL-184, VER-155008, CP-724714, NVP-AUY922, U-0126, forskolin, AZD-7762, 17-hydroxyprogesterone-caproate, purmorphamine, HSP90-inhibitor, daunorubicin, DMBI, SB-366791, QL-XI-92, imiquimod, sulfinpyrazone, sinensetin, BRD-K85853281, evodiamine, doxorubicin, rosuvastatin, GR-46611, geranylgeraniol, nifedipine, BRD-K71726959, prima-1-met, troglitazone, brivanib, and KIN001-055.

2. The method of claim 1, wherein the ABCs in the subject exhibiting the pathological capacity include the ABCs in the subject involved in cellular remodeling in the alveolar compartment of the lung.

3. The method of claim 1, wherein the subject suffers from a lung disease caused by the pathological capacity of the ABC for bronchosphere formation, and wherein the lung disease is characterized by a remodeling of alveolar epithelial cells and/or tissue, and that has not yet developed into a lung fibrosis.

4. The method of claim 1, wherein the compound is a c-Src inhibitor.

5. The method of claim 4, wherein the c-Src inhibitor is bosutinib, saracatinib, danusertib, VP-BHG712, quercetin, PCI-32765, KX2-391, AP23451 or dasatinib.

6. The method of claim 1, wherein the compound is not saracatinib.

7. The method of claim 6, wherein the compound is an Src-inhibitor.

8. The method of claim 6, wherein the compound is selected from the group consisting of bosutinib, danusertib, VP-BHG712, quercetin, PCI-32765, KX2-391, AP23451 and dasatinib.

9. The method of claim 1, wherein the subject is characterized by one or more of the following risk factors:
  (i) The subject is or was a smoker;
  (ii) The subject suffers from gastroesophageal reflux;
  (iii) The subject received or receives antidepressant drugs;
  (iv) The subject suffers from diabetes mellitus;
  (v) The subject was or is exposed to metal or wood dust environments;
  (vi) The subject suffers from a viral disease.

10. A method for identifying and/or characterizing a compound suitable for the treatment of a lung disease, the method comprising the steps of:
  (i) Providing at least one airway basal cell (ABC), optionally at least one lung fibroblast, and a candidate compound;
  (ii) Bringing into contact the at least one ABC, optionally the at least one lung fibroblast, and the candidate compound;
  (iii) Detecting and/or quantifying any one or a combination of the following screening markers: (a) formation of bronchospheres, (b) ABC proliferation and/or ABC viability, (c) when lung fibroblasts are used in (i) and (ii) fibroblast proliferation and/or collagen production;
  wherein a differential level of at least one screening marker as detected and/or quantified in (iii) when the least one ABC, optionally the at least lung fibroblast, are contacted with the candidate compound compared to when the least one ABC, optionally the at least one lung fibroblast, are not contacted with the candidate compound indicates the candidate compound as suitable for the treatment of the lung disease.

11. The method of claim 10, wherein the candidate compound is an c-Src inhibitor which is not saracatinib.

12. The method of claim 11, wherein the ABC and/or fibroblast are derived from a patient suffering from the lung disease selected from fibrosis or a pre-stage of lung fibrosis.

* * * * *